United States Patent
Baig et al.

(10) Patent No.: US 10,526,441 B1
(45) Date of Patent: Jan. 7, 2020

(54) POLYPYRROLE-COATED SILVER PARTICLES FOR SURFACE ENHANCED RAMAN SCATTERING

(71) Applicant: King Fahd University of Petroleum and Minerals, Dhahran (SA)

(72) Inventors: Umair Baig, Dhahran (SA); Mohammad Kamal Hossain, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 16/255,057

(22) Filed: Jan. 23, 2019

(51) Int. Cl.
| | |
|---|---|
| *G01J 3/44* | (2006.01) |
| *C08G 61/12* | (2006.01) |
| *G01N 21/65* | (2006.01) |
| *G01N 21/84* | (2006.01) |
| *B82Y 30/00* | (2011.01) |
| *B82Y 20/00* | (2011.01) |

(52) U.S. Cl.
CPC ......... *C08G 61/124* (2013.01); *G01N 21/658* (2013.01); *G01N 21/84* (2013.01); *B82Y 20/00* (2013.01); *B82Y 30/00* (2013.01); *C08G 2261/43* (2013.01); *C08G 2261/50* (2013.01); *C08G 2261/964* (2013.01)

(58) Field of Classification Search
CPC .............. C08G 61/124; C08G 2261/43; C08G 2261/964; C08G 2261/50; G01N 21/658; G01N 21/84; B82Y 20/00; B82Y 30/00
See application file for complete search history.

(56) References Cited

U.S. PATENT DOCUMENTS

2014/0185123 A1* 7/2014 Chen ................. G02F 1/155
359/265

FOREIGN PATENT DOCUMENTS

| CN | 104390950 A | 11/2014 |
|---|---|---|
| CN | 104599862 B | 1/2015 |
| CN | 107799325 A | 9/2017 |
| CN | 108010745 A | 1/2018 |

OTHER PUBLICATIONS

Salahuddin, et al. ; Antibacterial and anticancer activity of loaded quinazolinone polypyrrole/chitosan silver chloride nanocomposite ; International Journal of Polymeric Materials and Polymeric Biomaterials, vol. 66, Issue 6 ; Oct. 7, 2016 ; Abstract Only ; 2 Pages.

(Continued)

*Primary Examiner* — Abdullahi Nur
(74) *Attorney, Agent, or Firm* — Oblon, McClelland, Maier & Neustadt, L.L.P.

(57) ABSTRACT

A method of fabricating polypyrrole-coated silver particles having a core-shell structure via in-situ oxidative polymerization using silver nanoparticles and pyrrole monomers in the presence of an oxidizing agent. A surface enhanced Raman scattering (SERS) active substrate comprising the polypyrrole-coated silver particles is also disclosed. The surface enhanced Raman scattering (SERS) active substrate is demonstrated to facilitate the detection and measurement of surface enhanced Raman scattering (SERS) spectra of analytes with increased Raman signal intensity.

20 Claims, 8 Drawing Sheets

(56) References Cited

OTHER PUBLICATIONS

Ghadim, et al. ; Synthesis of PPy—silver nanocomposites via in situ oxidative polymerization ; J Nanostruct Chem ; Apr. 23, 2014 ; 5 Pages.

Ahmad, et al. ; Preparation and characterization of polypyrrole nanocomposites by using various surfactants and Fe O nanoparticles in aqueous media ; Journal of Vinyl & Additive Technology ; Dec. 1, 2014 ; Abstract Only ; 1 Page.

Men'Shikovs, et al. ; Synthesis of Polypyrrole Nanoparticles by Dispersion Polymerization ; Russian Journal of Applied Chemistry, vol. 75, Issue 5 ; pp. 822-826 ; 2003 ; 2 Pages.

Lie, et al. ; Evidence of Chemical Effect on Surface-Enhanced Raman Scattering of Polypyrrole Films Electrodeposited on Roughened Gold Substrates ; Langmuir 18 (1) ; pp. 174-181 ; Dec. 11, 2001 ; Abstract Only ; 1 Page.

Peng, et al. ; Facile preparation of water dispersible polypyrrole nanotubesupported silver nanoparticles for hydrogen peroxide reduction and surface-enhanced Raman scattering ; Electrochimica Acta vol. 75 ; pp. 399-405 ; Jul. 2012 ;Abstract Only ; 1 page.

\* cited by examiner

POLYPYRROLE-COATED SILVER PARTICLES FOR SURFACE ENHANCED RAMAN SCATTERING

BACKGROUND OF THE INVENTION

Technical Field

The present disclosure relates to a process of making polypyrrole-coated Ag particles via an in situ oxidative polymerization reaction, a surface enhanced Raman scattering (SERS) active substrate that includes the polypyrrole-coated Ag particles and analyte detection methods thereof.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Surface-enhanced Raman scattering (SERS), a subset of Raman spectroscopy, is a well-established ultrasensitive and nondestructive technique to detect chemical and biological molecules at very low concentrations, and even single molecules [Ozaki, Y.; Kneipp, K.; Ricardo Aroca. *Frontiers of Surface-Enhanced Raman Scattering: Single Nanoparticles and Single Cells*; John Wiley & Sons Ltd, Chichester, 2014; Hossain, M. K. Surface-Enhanced Raman Scattering: A Technique of Choice for Molecular Detection. *Mater. Sci. Forum* 2013, 754, 143-169; Pieczonka, N. P. W.; Moula, G.; Skarbek, A. R.; Aroca, R. F. Single-Molecule- and Trace Detection by SERS. In *Surface Enhanced Raman Spectroscopy*; Wiley-VCH Verlag GmbH & Co. KGaA: Weinheim, Germany, 2010; pp 87-101; Kneipp, K.; Kneipp, H.; Bohr, H. G. Single-Molecule SERS Spectroscopy. In *Surface-Enhanced Raman Scattering*; Springer Berlin Heidelberg, 2006; pp 261-277; Lee, H. M.; Jin, S. M.; Kim, H. M.; Suh, Y. D. Single-Molecule Surface-Enhanced Raman Spectroscopy: A Perspective on the Current Status. *Phys. Chem. Chem. Phys.* 2013, 15 (15), 5276; and Wang, Y.; Irudayaraj, J. Surface-Enhanced Raman Spectroscopy at Single-Molecule Scale and Its Implications in Biology. *Philos. Trans. R. Soc. Lond. B. Biol. Sci.* 2013, 368 (1611), 20120026]. The substrate/electrode underneath is believed to play a key role in providing a strong and localized electromagnetic field and thus enhancing scattered Raman photons up to the single molecule detection limit. In the SERS community, the term "hot spot" is defined as a strong electromagnetic field induced by close proximity of two plasmonic nanoparticles at the center of an interparticle gap. Importantly, the strong and localized electromagnetic field may be obtained from various plasmonic nanostructures of controlled sizes and morphologies [Hossain, M. K.; Kitajima, M.; Imura, K.; Okamoto, H. Near-Field Spectroscopy of Well-Defined Gold Nanoaggregate. 2012, 966 (0), 8-9; Hossain, M. K.; Kitajima, M.; Imura, K.; Okamoto, H. A Topography-Metrology Correlation in Nanoscale Probed by Near-Field Scanning Optical Microscopy. *Plasmonics* 2015, 10, 447-454; Imura, K.; Okamoto, H.; Hossain, M. K. Visualization of Localized Intense Optical Fields in Single Gold-Nanoparticle Assemblies and Ultrasensitive Raman Active Sites. *Nano Lett.* 2006, 6 (10), 2173-2176; and Hossain, M. K.; Kitajima, M.; Imura, K.; Okamoto, H. Interstitial-Dependent Enhanced Photoluminescence: A Near-Field Microscopy on Single Spheroid to Dimer, Tetramer, and Few Particles Gold Nanoassembly. *J. Phys. Chem. C* 2017, 121 (4), each incorporated herein by reference in their entirety]. To this end, a wide variety of processes are available in both physical and chemical routes, including plasma treatment, laser ablation in liquid, lithography, etc. for the preparation of such plasmonic nanostructures [Bai, L.; Jia, L.; Yan, Z.; Liu, Z.; Liu, Y. Plasma-Assisted Fabrication of Nanoparticle-Decorated Electrospun Nanofibers. *J. Taiwan Inst. Chem. Eng.* 2018, 82, 360-366; Park, S.-G.; Mun, C.; Xiao, X.; Braun, A.; Kim, S.; Giannini, V.; Maier, S. A.; Kim, D.-H. Surface Energy-Controlled SERS Substrates for Molecular Concentration at Plasmonic Nanogaps. *Adv. Funct. Mater.* 2017, 27 (41), 1703376; Zhao, X.; Wen, J.; Zhang, M.; Wang, D.; Wang, Y.; Chen, L.; Zhang, Y.; Yang, J.; Du, Y. Design of Hybrid Nanostructural Arrays to Manipulate SERS-Active Substrates by Nanosphere Lithography. *ACS Appl. Mater. Interfaces* 2017, 9 (8), 7710-7716; Yüksel, S.; Ziegler, M.; Goerke, S.; Huebner, U.; Weber, K.; Schaaf, P.; Meyer, H.-G.; Cialla-May, D.; Popp, J. Hierarchically-Designed 3D Flower-Like Composite Nanostructures as an Ultrastable, Reproducible, and Sensitive SERS Substrate. *ACS Appl. Mater. Interfaces* 2017, 9 (44), 38854-38862; and Durmanov, N. N.; Guliev, R. R.; Eremenko, A. V.; Boginskaya, I. A.; Ryzhikov, I. A.; Trifonova, E. A.; Putlyaev, E. V.; Mukhin, A. N.; Kalnov, S. L.; Balandina, M. V.; et al. Non-Labeled Selective Virus Detection with Novel SERS-Active Porous Silver Nanofilms Fabricated by Electron Beam Physical Vapor Deposition. *Sensors Actuators B Chem.* 2018, 257, 37-47, each incorporated herein by reference in their entirety]. In addition to metal and bimetal nanoparticles, there is a large collection of plasmonic nanostructures reported so far, such as core-shell nanoparticles, corrugated metal substrates, porous substrates, coated flower petals, etc. [Zhao, X.; Wen, J.; Zhang, M.; Wang, D.; Wang, Y.; Chen, L.; Zhang, Y.; Yang, J.; Du, Y. Design of Hybrid Nanostructural Arrays to Manipulate SERS-Active Substrates by Nanosphere Lithography. *ACS Appl. Mater. Interfaces* 2017, 9 (8), 7710-7716; Yüksel, S.; Ziegler, M.; Goerke, S.; Huebner, U.; Weber, K.; Schaaf, P.; Meyer, H.-G.; Cialla-May, D.; Popp, J. Hierarchically-Designed 3D Flower-Like Composite Nanostructures as an Ultrastable, Reproducible, and Sensitive SERS Substrate. *ACS Appl. Mater. Interfaces* 2017, 9 (44), 38854-38862; Durmanov, N.; Guliev, R. R.; Eremenko, A. V.; Boginskaya, I. A.; Ryzhikov, I. A.; Trifonova, E. A.; Putlyaev, E. V.; Mukhin, A. N.; Kalnov, S. L.; Balandina, M. V.; et al. Non-Labeled Selective Virus Detection with Novel SERS-Active Porous Silver Nanofilms Fabricated by Electron Beam Physical Vapor Deposition. *Sensors Actuators B Chem.* 2018, 257, 37-47; Yang, X.; Guo, W.; Wang, X.; Liao, M.; Gao, P.; Ye, J. Fabrication of Highly Ordered 2D Metallic Arrays with Disc-in-Hole Binary Nanostructures via a Newly Developed Nanosphere Lithography. *Nanotechnology* 2017, 28 (47), 474001; Liu, C.; Tan, L.; Li, L.; Dong, J.; Qian, W. Two-in-One: Au Nanocages with a Highly Open Architecture and "hotspot" Effect as SERS-Active Substrates. *Cryst Eng Comm* 2017, 19 (24), 3233-3236; Ghosh Chaudhuri, R.; Paria, S. Core/Shell Nanoparticles: Classes, Properties, Synthesis Mechanisms, Characterization, and Applications. *Chem. Rev.* 2012, 112 (4), 2373-2433; and Shen, W.; Lin, X.; Jiang, C.; Li, C.; Lin, H.; Huang, J.; Wang, S.; Liu, G.; Yan, X.; Zhong, Q.; et al. Reliable Quantitative SERS Analysis Facilitated by Core-Shell Nanoparticles with Embedded Internal Standards. *Angew. Chemie Int. Ed.* 2015, 54 (25), 7308-7312, each incorporated herein by reference in their entirety]. However, processes for preparing these plasmonic nanostructures require sophisticated, state-of-art facilities and experienced personnel. The complexity of these processes can cause contaminations that hinder SERS activity of the nanostructures.

Polypyrrole (PPy) is attractive because of its electrical conductivity, resistivity to degradation, low cost, and straightforward synthesis [Yao, H.; Zhang, F.; Zhang, G.; Luo, H.; Liu, L.; Shen, M.; Yang, Y. A Novel Two-Dimensional Coordination Polymer-Polypyrrole Hybrid Material as a High-Performance Electrode for Flexible Supercapacitor. *Chem. Eng. J* 2018, 334, 2547-2557; Li, C.; Bai, H.; Shi, G. Conducting Polymer Nanomaterials: Electrosynthesis and Applications. *Chem. Soc. Rev.* 2009, 38 (8), 2397; Liu, K.; Li, Y.; Zhang, H.; Liu, Y. Synthesis of the Polypyrrole Encapsulated Copper Nanowires with Excellent Oxidation Resistance and Temporal Stability. *Appl. Surf Sci.* 2018, 439, 226-231; and Hosseini, M.; Fotouhi, L.; Ehsani, A.; Naseri, M. Enhancement of Corrosion Resistance of Polypyrrole Using Metal Oxide Nanoparticles: Potentiodynamic and Electrochemical Impedance Spectroscopy Study. *J. Colloid Interface Sci.* 2017, 505, 213-219, each incorporated herein by reference in their entirety]. However, studies on PPy as SERS-active substrate are very scarce [Jeong, D.-W.; Jeong, S.; Jang, D.-J. One-Step Polypyrrole Coating of Self-Assembled Silver Nanoprisms for Enhanced Stability and Raman Scattering. *J. Nanoparticle Res.* 2017, 19 (7), 249; and Zhou, S.; Wang, M.; Chen, X.; Xu, F. Facile Template Synthesis of Microfibrillated Cellulose/Polypyrrole/Silver Nanoparticles Hybrid Aerogels with Electrical Conductive and Pressure Responsive Properties. *ACS Sustain. Chem. Eng.* 2015, 3 (12), 3346-3354, each incorporated herein by reference in their entirety]. Most studies have used PPy as a base material or a reducing agent for the synthesis of plasmonic nanostructures including silver, gold, and platinum nanoparticles. In these situations, the plasmonic nanoparticles are often labile when exposed to the surrounding environment and eventually lose SERS activity [Chang, Y.-H.; Hsu, W.-H.; Wu, S.-L.; Ding, Y.-C. The Synthesis of a Gold Nanodisk-molecular Layer-gold Film Vertical Structure: A Molecular Layer as the Spacer for SERS Hot Spot Investigations. *Mater. Chem. Front.* 2017, 1 (5), 922-927; Zhang, L.; Liu, X.; Wang, Y.; Xing, S. Controllable Silver Embedding into Polypyrrole. *J. Alloys Compd.* 2017, 709, 431-437; and He, Y.; Han, X.; Chen, D.; Kang, L.; Jin, W.; Qiang, R.; Xu, P.; Du, Y. Chemical Deposition of Ag Nanostructures on Polypyrrole Films as Active SERS Substrates. *RSC Adv.* 2014, 4 (14), 7202, each incorporated herein by reference in their entirety]. It was reported that Ag coated PPy microparticles provided strong SERS activity using 4-mercaptopyridine as a dye and PPy as a base, and Ag nanoparticles were decorated on the surface of PPy [Wang, W.; Li, W.; Zhang, R. Controlled Fabrication of Surface-Enhanced-Raman Scattering-Active Silver Nanostructures on Polypyrrole Films. *Mater. Chem. Phys.* 2010, 124 (1), 385-388; and Wang, W.; Zhang, R. Silver-polypyrrole Composites: Facile Preparation and Application in Surface-Enhanced Raman Spectroscopy. *Synth. Met.* 2009, 159 (13), 1332-1335, each incorporated herein by reference in their entirety]. In this situation, PPy decorated by Ag nanoparticles may be a suitable SERS-active substrate; however silver rapidly undergoes oxidation and loses relevant properties required for SERS-active substrates.

PPy may be used in ways different from those reported in previous attempts. For example, PPy-coated plasmonic nanoparticles may be used as a potential candidate in various applications including molecule detection, sensor, optoelectronics, plasmonics, photonics, and optical switching. However, PPy-coated silver spherical particles have not been demonstrated to act as SERS-active substrate for molecule detection.

In view of the forgoing, one objective of the present disclosure is to provide a simple chemical oxidative polymerization route to produce polypyrrole-coated Ag particles. Another objective of the present disclosure is to provide a surface enhanced Raman scattering (SERS) active substrate comprising the polypyrrole-coated Ag particles. A further aim of the present disclosure is to provide a strategy for detecting and measuring SERS data of an analyte by employing the surface enhanced Raman scattering (SERS) active substrate. The strategy reported herewith opens up the way to a new design of polymer-based core-shell nanomaterials for a wide range of applications.

BRIEF SUMMARY OF THE INVENTION

According to a first aspect, the present disclosure relates to a method of producing polypyrrole-coated Ag particles in the form of spheres and comprising a silver core and a polypyrrole shell, wherein at least a portion of the surface of the silver core is coated by the polypyrrole shell. The method involves mixing silver nanoparticles with an aqueous solution of pyrrole to form a mixture comprising pyrrole-adsorbed silver nanoparticles, and mixing an oxidizing agent with the mixture to polymerize the pyrrole of the pyrrole-adsorbed silver nanoparticles, thereby forming the polypyrrole-coated Ag particles.

In one embodiment, the pyrrole is polymerized at 4-40° C.

In one embodiment, a molar ratio of the pyrrole to the silver nanoparticles is 5:1 to 150:1.

In one embodiment, the oxidizing agent is $FeCl_3$.

In one embodiment, a molar ratio of $FeCl_3$ to the silver nanoparticles is 5:1 to 150:1.

In one embodiment, the method further involves drying the polypyrrole-coated Ag particles at a temperature of 50-100° C.

In one embodiment, the silver core has an average diameter of 50-200 nm, and the polypyrrole shell has an average thickness of 25-80 nm.

In one embodiment, the polypyrrole-coated Ag particles are not angular shaped.

In one embodiment, the polypyrrole-coated Ag particles have an average diameter of 100-360 nm.

In one embodiment, the polypyrrole-coated Ag particles have a UV-vis absorption of 350-800 nm.

In one embodiment, the mixture is devoid of polyvinyl pyrrolidone.

According to a second aspect, the present disclosure relates to a surface enhanced Raman scattering (SERS) active substrate, comprising a glass layer and polypyrrole-coated Ag particles immobilized on the glass layer, wherein the polypyrrole-coated Ag particles are in the form of spheres, and comprise a silver core with a diameter of 50-200 nm and a polypyrrole shell with a thickness of 25-80 nm, and wherein at least a portion of the surface of the silver core is coated by the polypyrrole shell.

In one embodiment, the surface enhanced Raman scattering (SERS) active substrate has a SERS enhancement factor of $10^4$-$10^{10}$.

In one embodiment, the polypyrrole-coated Ag particles are produced by a method involving mixing silver nanoparticles with an aqueous solution of pyrrole to produce a mixture comprising pyrrole-adsorbed silver nanoparticles, and mixing an oxidizing agent with the mixture to polymerize the pyrrole of the pyrrole-adsorbed silver nanoparticles, thereby forming the polypyrrole-coated Ag particles.

In one embodiment, the surface enhanced Raman scattering (SERS) active substrate further contains nanoparticles comprising at least one metal selected from the group consisting of gold, copper, aluminum, platinum, palladium, and alloys thereof immobilized on the glass layer.

According to a third aspect, the present disclosure relates to a method for measuring surface enhanced Raman scattering (SERS) signal of an analyte. The method involves the steps of contacting the analyte with the surface enhanced Raman scattering (SERS) active substrate of the second aspect to prepare a sample, exciting the sample with a light source to produce a Raman signal, and detecting and measuring the Raman signal of the sample, wherein the analyte has a Raman signal that is enhanced relative to that of the analyte without the surface enhanced Raman scattering (SERS) active substrate.

In one embodiment, the analyte contains at least one biological molecule selected from the group consisting of a protein, a deoxyribonucleic acid sequence, a ribonucleic acid sequence, an amino acid, a peptide, a nucleotide, a nucleoside, and a neurotransmitter.

In one embodiment, the analyte contains at least one synthetic molecule.

In one embodiment, the analyte comprises Rhodamine 6G.

In one embodiment, the method has a surface enhanced Raman scattering (SERS) detection limit of the analyte at a concentration of $1\times10^{-10}$-$1\times10^{-8}$ M.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
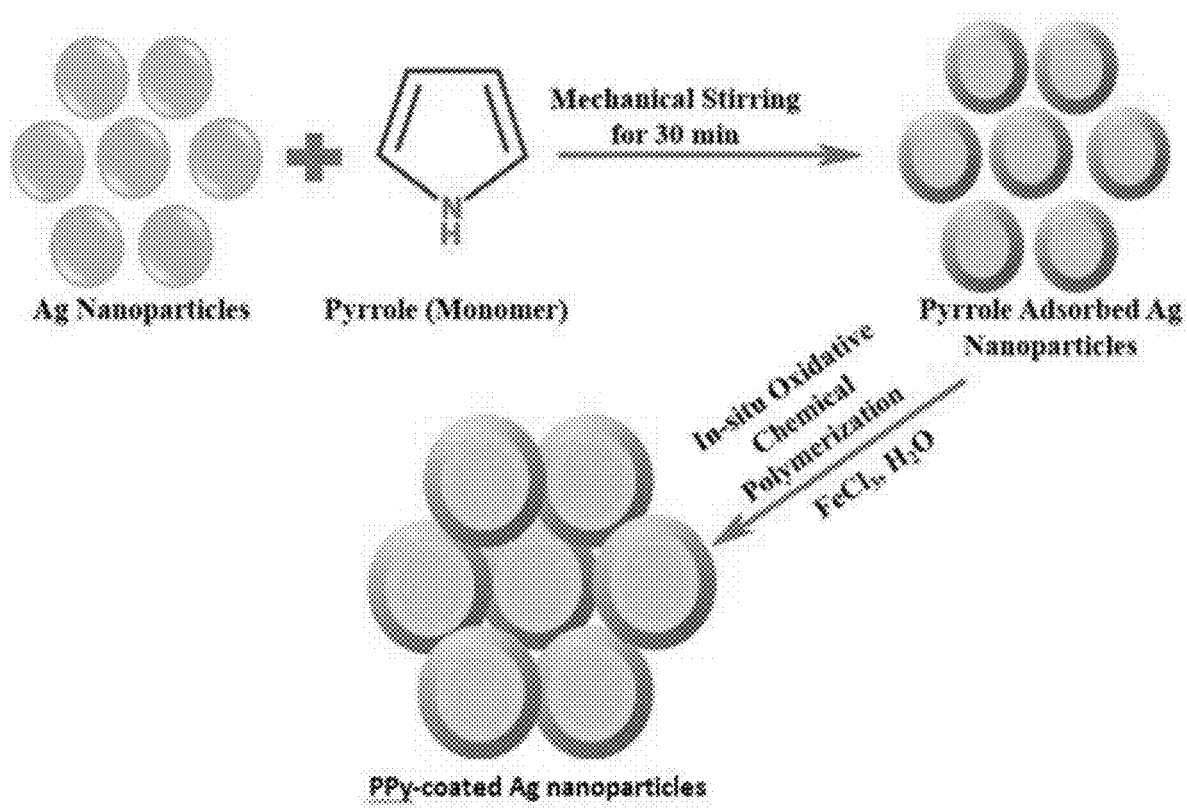
FIG. 1 is a schematic diagram showing the preparation of polypyrrole-coated (PPy-coated) Ag particles.
Figure 2A:
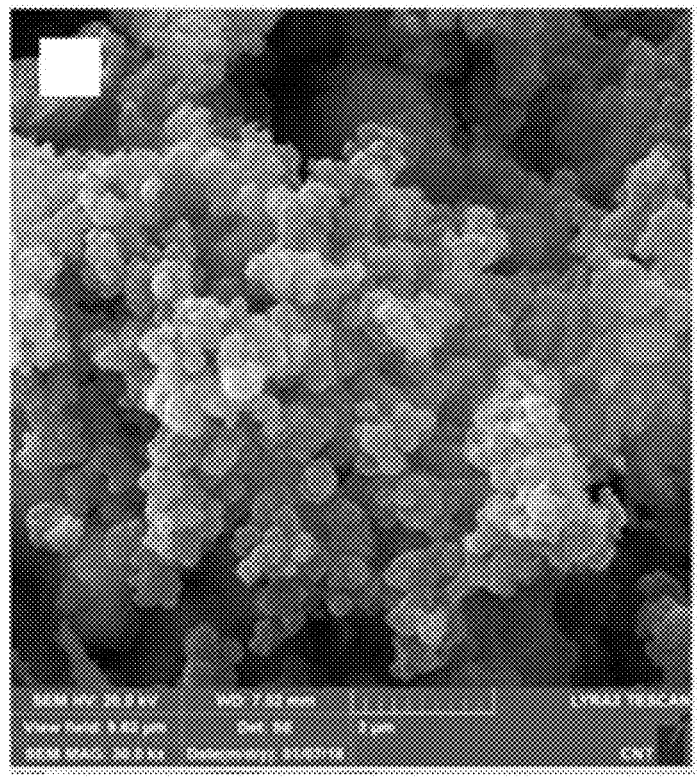
FIG. 2A is a field-emission scanning electron microscopy (FE-SEM) image of the prepared PPy-coated Ag particles.
Figure 2B:
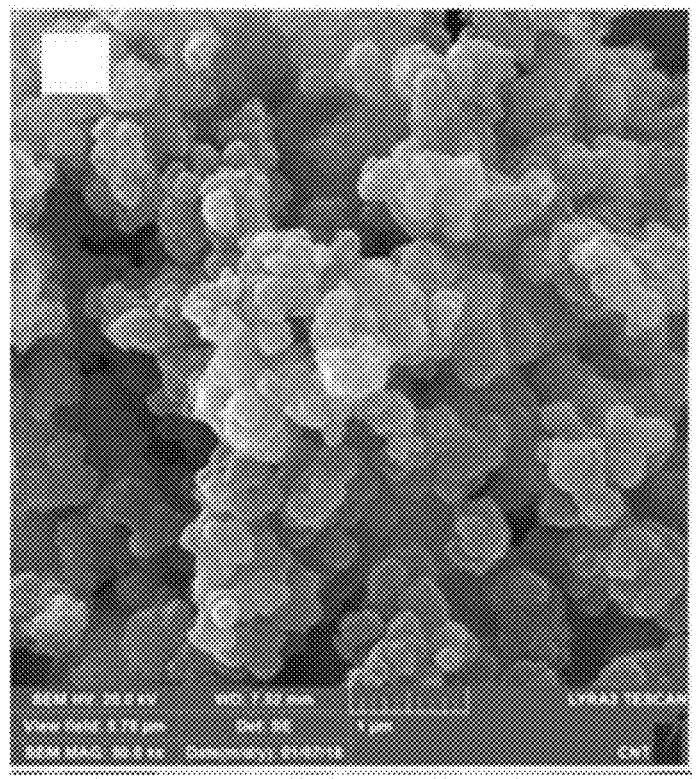
FIG. 2B is a FE-SEM image of a magnified view of a segment of the PPy-coated Ag particles of FIG. 2A.
Figure 2C:
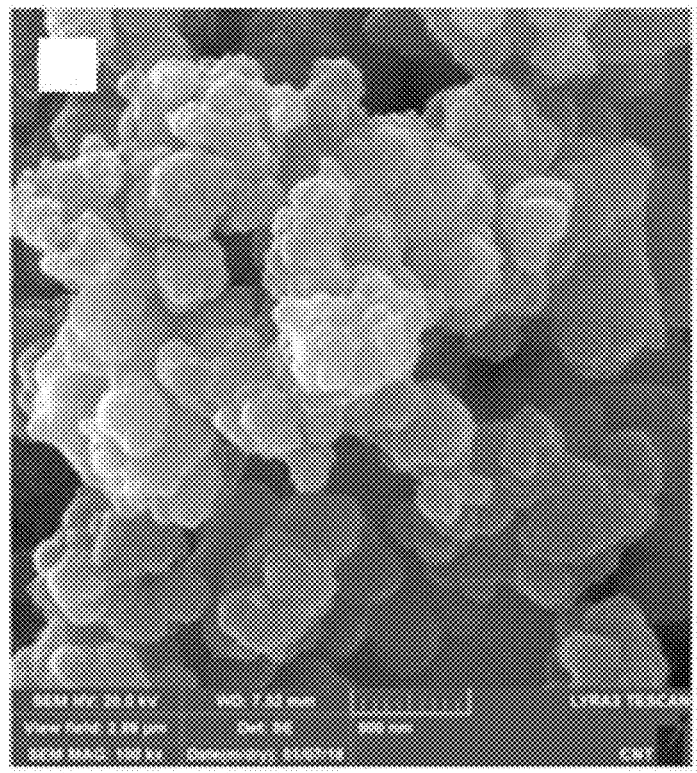
FIG. 2C is a FE-SEM image of a magnified view of a segment of the PPy-coated Ag particles of FIG. 2B.
Figure 2D:
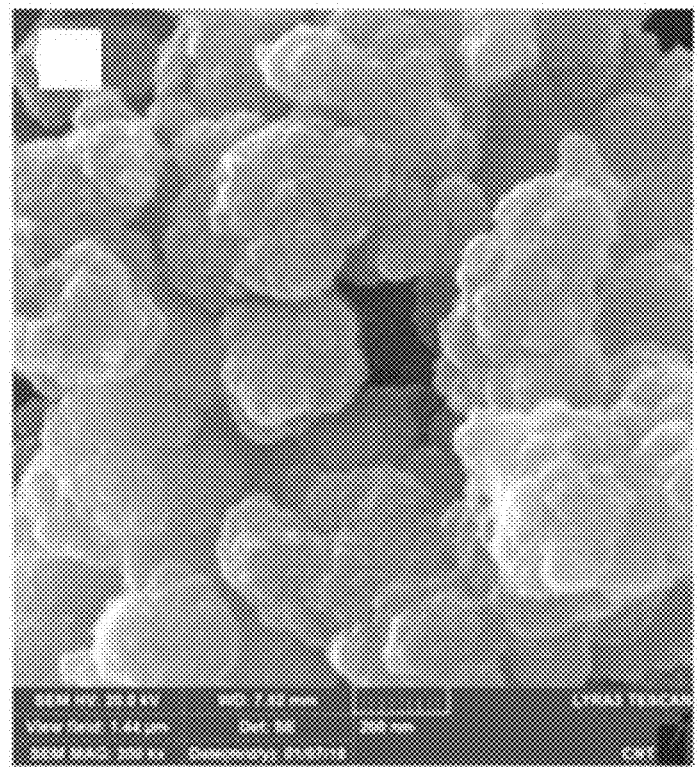
FIG. 2D is a FE-SEM image of a magnified view of a segment of the PPy-coated Ag particles of FIG. 2C.

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, iso-butanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those skilled in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the double bonds, ring systems, stereogenic centers, and the like can all be present in the compounds, and all such stable isomers are contemplated in the present disclosure. Cis- and trans- (or E- and Z-) stereoisomers of the compounds of the present disclosure wherein rotation around the double bond is restricted, keeping the substituents fixed relative to each other, are described and may be isolated as a mixture of isomers or as separated isomeric forms. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, aubstituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, carbamyl (e.g. —CONH$_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like. The substituents may themselves be optionally substituted, and may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

As used herein, the term "alkyl" unless otherwise specified refers to both branched and straight chain saturated aliphatic primary, secondary, and/or tertiary hydrocarbons of typically $C_1$ to $C_{20}$, for example $C_1$, $C_2$, $C_3$, $C_4$, $C_5$, $C_6$, $C_7$, $C_8$, $C_9$, $C_{10}$, $C_{11}$, $C_{12}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl.

The term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "arylalkyl", as used herein, refers to a straight or branched chain alkyl moiety having 1 to 8 carbon atoms that is substituted by an aryl group as defined herein, and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

As used herein, the term "aryl" unless otherwise specified refers to functional groups or substituents derived from an aromatic ring including, but not limited to, phenyl, biphenyl, napthyl, thienyl, and indolyl. As used herein, the term optionally includes both substituted and unsubstituted moieties. Exemplary moieties with which the aryl group can be substituted may be selected from the group including, but not limited to, hydroxyl, amino, alkylamino, arylamino, alkoxy, aryloxy, nitro, cyano, sulfonic acid, sulfate, phosphonic acid, phosphate or phosphonate or mixtures thereof. The substituted moiety may be either protected or unprotected as necessary, and as known to those skilled in the art.

The term "alkanoyl" refers to an alkyl group of specified number of carbon atoms that is bound to an oxygen atom through a double bond. Exemplary alkanoyl groups include, but are not limited to, formyl, acetyl, propanoyl, butyryl, and hexanoyl.

The term "aroyl" as used in this disclosure refers to an aromatic carboxylic acyl group includes, for example, benzoyl, 1-naphthoyl, and 2-naphthoyl.

The term "halogen", as used herein, means fluoro, chloro, bromo and iodo.

The present disclosure is further intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}C$ and $^{14}C$, isotopes of nitrogen include $^{14}N$ and $^{15}N$, isotopes of oxygen include $^{16}O$, $^{17}O$ and $^{18}O$, and isotopes of silver include $^{107}Ag$ and $^{109}Ag$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

According to a first aspect, the present disclosure relates to a method of producing polypyrrole-coated Ag particles in the form of spheres and comprising a silver core and a polypyrrole shell, wherein at least a portion of the surface of the silver core is coated by the polypyrrole shell. The method involves mixing silver nanoparticles with an aqueous solution of pyrrole to form a mixture comprising pyrrole-adsorbed silver nanoparticles, and mixing an oxidizing agent with the mixture to polymerize the pyrrole of the pyrrole-adsorbed silver nanoparticles, thereby forming the polypyrrole-coated Ag particles.

Silver (Ag) is a precious metal element exhibiting a face centered cubic crystal structure. It is a soft, white, and lustrous transition metal that possesses the highest electrical conductivity, thermal conductivity and reflectivity of any metal. The metal occurs naturally in its pure, free form (native silver), as an alloy with gold and other metals, and in minerals such as argentite and chlorargyrite. Most silver is produced as a byproduct of copper, gold, lead, and zinc refining. Naturally occurring silver is composed of two stable isotopes $^{107}Ag$ and $^{109}Ag$ with almost equal abundance.

As defined herein, silver nanoparticles refer to particles of silver of between 1-500 nm in size. Although frequently described as silver, they may be comprised of a large percentage of silver oxide due to their large ratio of surface to bulk silver atoms. The most common oxidation state of silver is Ag(I) (e.g. silver nitrate, $AgNO_3$, silver(I) oxide, $Ag_2O$). Silver may exist in other oxidation states including Ag(II) (e.g. silver(II) fluoride, $AgF_2$), and Ag(III). In a preferred embodiment, the silver nanoparticles used herein substantially comprise elemental silver. The term "silver nanoparticle" as used herein refers to an elemental silver rich material (i.e. greater than 50%, more preferably greater than 60%, more preferably greater than 70%, more preferably greater than 75%, more preferably greater than 80%, more preferably greater than 85%, more preferably greater than 90%, more preferably greater than 95%, more preferably greater than 99% elemental silver by weight).

The exceptionally high surface area to volume ratio of nanoparticles may cause the nanoparticles to exhibit significantly different or even novel properties from those observed in individual atoms/molecules, fine particles and/or bulk materials. In a preferred embodiment, the silver nanoparticles used herein are in the form of nanoparticles, which are spherical or substantially spherical (e.g. oval, oblong, etc.) in shape. Alternatively, it is envisaged that the silver nanoparticles may have a more polygonal shape and may be generally cubic or rectangular. However, the silver nanoparticles used herein may have various shapes other than spheres and may be of any shape that provides desired surface enhanced Raman scattering (SERS) activity and/or desired properties in the resulting SERS active substrate. In a most preferred embodiment, the silver nanoparticles have a spherical morphology. Alternatively, the silver nanoparticles of the present disclosure are envisaged to demonstrate a variety of morphologies including, but not limited to, nanoparticles, nanosheets, nanoplatelets, nanocrystals, nanospheres, nanohexagons, nanodisks, nanocubes, nanowires, nanofibers, nanoribbons, nanorods, nanotubes, nanocylinders, nanogranules, nanowhiskers, nanoflakes, nanofoils, nanopowders, nanoboxes, nanostars, tetrapods, nanobelts, nanaourchins, nanofloweres, and mixtures thereof. In a preferred embodiment, at least 95% of a total population of the silver nanoparticles used herein is in the form of nanospheres, preferably at least 96%, preferably 97%, preferably 98%, preferably 99%, preferably 99.5% of the total population of the silver nanoparticles is in the form of nanospheres. In another preferred embodiment, less than 5% of the total population of the silver nanoparticles is in the form of nanoprisms, preferably less than 4%, preferably less than 3%, preferably less than 2%, preferably less than 1%, preferably less than 0.5% of the total population of the silver nanoparticles is in the form of nanoprisms.

For spherical or substantially spherical silver nanoparticles, average particle size refers to the average longest linear diameter of the nanoparticles. For non-spherical silver nanoparticles, such as cubes, squares and/or rectangles the average particle size may refer to the longest linear dimension and any of the length, width or height. In a preferred embodiment, the silver nanoparticles used herein are in the form of spheres and have an average particle size of 50-200 nm, preferably 60-150 nm, preferably 70-120 nm, preferably 80-110 nm, preferably 90-100 nm.

In a preferred embodiment, the silver nanoparticles used herein are monodisperse, having a coefficient of variation or relative standard deviation, expressed as a percentage and defined as the ratio of the particle size standard deviation (a) to the particle size mean (t) multiplied by 100 of less than 25%, preferably less than 10%, preferably less than 8%, preferably less than 6%, preferably less than 5%, preferably less than 4%, preferably less than 3%, preferably less than 2%. In a preferred embodiment, the silver nanoparticles used herein are monodisperse having a particle size distribution ranging from 80% of the average particle size to 120% of the average particle size, preferably 90-110%, preferably 95-105% of the average particle size.

In one or more embodiments, the pyrrole used herein is of formula (I)

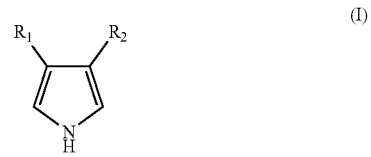

or a salt thereof, a solvate thereof, a tautomer thereof, a stereoisomer thereof, or a mixture thereof, wherein $R_1$ and $R_2$ are each independently selected from the group consisting of a hydrogen, an optionally substituted alkyl, an optionally substituted cycloalkyl, an optionally substituted arylalkyl, an optionally substituted aryl, an optionally substituted alkanoyl, and an optionally substituted aroyl, a halogen, and a cyano. In a preferred embodiment, $R_1$ and $R_2$ are each independently a hydrogen or an optionally substituted alkyl. Most preferably, each $R_1$ and $R_2$ are a hydrogen.

The method of producing the polypyrrole-coated Ag particles involves mixing silver nanoparticles with an aqueous solution of pyrrole to form a mixture comprising pyrrole-adsorbed silver nanoparticles. In one embodiment, the aqueous solution of pyrrole comprises water and pyrrole of formula (I). The water may be tap water, distilled water, bidistilled water, deionized water, deionized distilled water, reverse osmosis water, and/or some other water. In one embodiment, the water is bidistilled to eliminate trace metals. Preferably the water is bidistilled, deionized, deionized distilled, or reverse osmosis water. Most preferably the water is deionized water. The mixing may occur via stirring, shaking, sonicating, blending, or by otherwise agitating the mixture. Preferably the mixture is stirred for 0.1-6 hours, preferably 0.25-3 hours, preferably 0.5-2 hours. In one embodiment, one component (e.g. the silver nanoparticles) may be dispersed or mixed in the water by sonication for 10-180 min, preferably 20-90 min, preferably 30-60 min, or about 45 min first, and then other components (e.g. pyrrole) may be added and mixed via stirring. In one or more embodiments, a molar ratio of the pyrrole to the silver nanoparticles is 5:1 to 150:1, preferably 10:1 to 100:1, more preferably 20:1 to 50:1. However, in certain embodiments, the molar ratio of the pyrrole to the silver nanoparticles is less than 5:1 or greater than 150:1.

The aforementioned mixing of pyrrole and silver nanoparticles may lead to the formation of pyrrole-adsorbed silver nanoparticles comprising pyrrole molecules of formula (I) bound to a surface of the silver nanoparticles. As used herein, "adsorbed", "adsorbing", "bound", or "binding" refers to physisorption or chemisorption and mixtures thereof via strong atomic bonds (e.g. ionic, metallic, covalent bonds) and/or weak bonds such as van der Waals interactions and hydrogen bonds. In one embodiment, the pyrrole molecules are adsorbed onto a surface of the silver nanoparticles via metal-π interactions and/or electrostatic forces. In a related embodiment, additional pyrrole molecules may be adsorbed onto the pyrroles already bound to the surface of the silver nanoparticles via non-covalent interactions such as π-π stacking and hydrogen bonding. In preferred embodiments, the pyrrole-adsorbed silver nanoparticles have pyrrole molecules covering greater than 50%, greater than 60%, greater than 70%, greater than 80%, greater than 90%, greater than 95%, greater than 96%, greater than 97%, greater than 98%, greater than 99%, or greater than 99.5% of the total surface of the silver nanoparticles.

As described herein, the term "repeat unit" or "repeating unit" refers to a part of the polymer whose repetition would produce the complete polymer chain (including or excluding the end groups) by linking the repeating units together successively along the chain. Monomers are molecules which can undergo polymerization, thereby contributing constitutional repeating units to the structures of a macromolecule or polymer. The process by which monomers combine end to end to form a polymer is referred to herein as "polymerization" or "polymerizing".

Polypyrrole (PPy), which is an organic polymer formed by the polymerization of pyrrole monomers, belongs to an important class of conductive polymers. Polypyrroles may be prepared by oxidative polymerization of pyrroles. The polymerization process may start from the generation of radical cations of pyrrole molecules via single electron oxidation, followed by coupling of the radical cations to form a bipyrrole unit, and subsequent reaction with another radical cation to generate a reactive intermediate. Propagation of the polypyrrole chain at the final step (i.e. generation and subsequent coupling of reactive intermediates) continues until reactive intermediates are consumed. The radical cations of pyrrole monomers may be generated chemically using an oxidizing agent including, but not limited to, ferric chloride ($FeCl_3$), ferric bromide ($FeBr_3$), ferric nitrate ($Fe(NO_3)_3$), iron(III) perchlorate ($Fe(ClO_4)_3$), potassium ferricyanide ($K_3[Fe(CN)_6]$), potassium dichromate ($K_2Cr_2O_7$), potassium iodate ($KIO_3$), ammonium persulfate (or ammonium peroxydisulfate, $(NH_4)_2S_2O_8$), copper(II) chloride ($CuCl_2$), copper(II) bromide ($CuBr_2$), and hydrogen peroxide ($H_2O_2$). In preferred embodiments, the oxidizing agent is $FeCl_3$. Alternatively, the oxidation may be achieved electrochemically by applying an oxidizing potential.

The method of producing the polypyrrole-coated Ag particles also involves the step of mixing an oxidizing agent with the mixture to polymerize the pyrrole of the pyrrole-adsorbed silver nanoparticles, thereby forming the polypyrrole-coated Ag particles. The mixing of the oxidizing agent and the mixture may occur via stirring, shaking, sonicating, blending, or by otherwise agitating. Preferably the polymerizing is carried out by stirring for 1-72 hours, preferably 6-48 hours, preferably 12-36 hours, or about 24 hours at a temperature of 4-60° C., preferably 10-40° C., more preferably 20-30° C. Though in some embodiments, the polymerizing may occur at a temperature lower than 4° C. or higher than 60° C. Also, depending on the chemical reactivity of the oxidizing agent, the polymerizing may be carried out in vacuum, or under an inert gas such as $N_2$, Ar, and He.

In one or more embodiment, where $FeCl_3$ is used as the oxidizing agent, a molar ratio of $FeCl_3$ to the silver nanoparticles is 5:1 to 150:1, preferably 10:1 to 100:1, more preferably 20:1 to 50:1. However, in certain embodiments, the molar ratio of $FeCl_3$ to the silver nanoparticles is less than 5:1 or greater than 150:1. In a related embodiment, a molar ratio of $FeCl_3$ to the pyrrole is 1:10 to 10:1, preferably 1:5 to 5:1, more preferably 1:2 to 2:1, or about 1:1. In some embodiments, the molar ratio of $FeCl_3$ to the pyrrole is less than 1:10 or greater than 10:1.

In one embodiment, the polypyrrole-coated Ag particles are collected as a solid that may be separated (filtered off) from the aforementioned mixture, washed in water, and then filtered. In one or more embodiments, the method further involves drying the polypyrrole-coated Ag particles at a temperature of 50-100° C., preferably 60-90° C., more preferably 65-80° C., or about 70° C. for 0.5-8 hours, 1-4 hours, or 2-3 hours, though in some embodiments, the polypyrrole-coated Ag particles may be dried at a temperature lower than 50° C. or greater than 100° C. Preferably, this drying step involves the removal of the water, other solvents, and/or unreacted components.

Water soluble polymers such as polyvinyl pyrrolidone (PVP) and polyvinyl alcohol (PVA) are conventionally employed as phase stabilizers for the chemical oxidative polymerization of pyrrole monomers in an aqueous environment. However, it is worth mentioning that these water soluble polymer stabilizers are difficult to be removed completely from the produced polypyrrole due to the strong affinity between the polypyrrole and the stabilizers. For SERS applications, residual water soluble polymer stabilizers may prevent Raman analytes from coming close to the center of the interparticle gaps or hot spots. In addition, these phase stabilizers may induce a huge background emission, which is unfavorable for the specific detection of analytes. In one embodiment, the mixture of the currently disclosed method comprises substantially no water soluble polymers, for instance, less than 0.1 wt % of water soluble polymers, preferably less than 0.05 wt %, more preferably less than 0.01 wt % of water soluble polymers, relative to a total weight of the mixture. In at least one embodiment, the mixture is devoid of polyvinyl pyrrolidone.

In one embodiment, the polypyrrole produced herein is a linear chain polymer with a weight-average molecular weight in the range of 1,000 to 500,000 Da, preferably 5,000 to 100,000 Da, preferably 10,000 to 80,000 Da, preferably 20,000 to 60,000 Da, preferably 30,000 to 50,000 Da. In some embodiments, a portion of the polypyrrole may be present in a non-linear polymer form, e.g. in a form of a brushed polymer, a branched polymer, or a crosslinked polymer. Preferably, a non-linear portion of the polypyrrole is no more than 10 wt %, preferably no more than 5 wt %, more preferably no more than 2 wt %, relative to a total weight of the polypyrrole.

A particle is defined as a small object that behaves as a whole unit with respect to its transport and properties. The polypyrrole-coated Ag particles of the present disclosure in any of its embodiments may be of the same shape or different shapes, and of the same size or different sizes. An average diameter (e.g., average particle diameter) of the particle, as used herein, refers to the average linear distance measured from one point on the particle through the center of the particle to a point directly across from it. Unless defined elsewhere, nanoparticles are particles having an average diameter between 1 and 100 nm in size. Microparticles are particles having an average diameter between 0.1 and 100 gpm in size. The size and shape of particles may be analyzed by techniques such as dynamic light scattering (DLS), scanning electron microscopy (SEM), transmission electron microscopy (TEM), and/or atomic force microscopy (AFM).

In one or more embodiments, the polypyrrole-coated Ag particles produced herein may be spherical, ellipsoidal, oblong, ovoidal, or some other rounded shape. In a preferred embodiment, the polypyrrole-coated Ag particles are substantially in the form of spheres, meaning that the distance from the particle centroid (center of mass) to anywhere on the outer surface of the particle varies by less than 25%, preferably by less than 20%, more preferably by less than 10% of the average distance.

In one embodiment, the polypyrrole-coated Ag particles produced herein may be nanoparticles having an average diameter in a range of 1-99 nm, 5-90 nm, 10-80 nm, 20-70 nm, 30-60 nm, or 40-50 nm. In another embodiment, the polypyrrole-coated Ag particles may be microparticles having an average diameter in a range of 0.1-50 μm, 0.2-25 μm, 0.3-10 μm, 0.4-5 μm, 0.5-2 μm, or 1-1.5 μm. In a preferred embodiment, the polypyrrole-coated Ag particles produced herein are in the form of spheres and have an average diameter of 100-360 nm, 120-350 nm, 150-320 nm, 180-300 nm, or 200-250 nm.

In one or more embodiments, the polypyrrole-coated Ag particles described herein are not angular shaped, for instance, less than 5% of a total population of the polypyrrole-coated Ag particles is angular shaped, preferably less than 4%, preferably less than 3%, preferably less than 2%, preferably less than 1%, preferably less than 0.5% of the total population of the polypyrrole-coated Ag particles is angular shaped. Examples of angular shapes include rectangles, triangles, pentagons, prisms, prismoids, or some other angular shapes. In at least one embodiment, the polypyrrole-coated Ag particles described herein are not in the form of nanoprisms. As defined herein, the term "nanoprisms" refers to nanoparticles that exhibit prismatic properties and typically have a triangular shape with an edge length as well as a thickness that can optionally have rounded or truncated corners. Nanoprisms are anisotropic. On the contrary, "spheres", "nanospheres", and "microspheres" have spherical structure and are isotropic.

Preferably, the polypyrrole-coated Ag particles produced herein have a "core-shell" structure which includes a silver core (e.g. the silver nanoparticles) and a polypyrrole shell. In one embodiment, the silver core substantially comprises elemental silver. For example, the silver core may contain greater than 50%, preferably greater than 60%, more preferably greater than 70%, more preferably greater than 75%, more preferably greater than 80%, more preferably greater than 85%, more preferably greater than 90%, more preferably greater than 95%, more preferably greater than 99% elemental silver by weight. In another embodiment, the silver core substantially comprises silver oxide (e.g. $Ag_2O$). For example, the silver core may contain greater than 50%, preferably greater than 60%, more preferably greater than 70%, more preferably greater than 75%, more preferably greater than 80%, more preferably greater than 85%, more preferably greater than 90%, more preferably greater than 95%, more preferably greater than 99% silver oxide by weight. Alternatively, the silver core prepared herein may contain a mixture of elemental silver and silver oxide at a weight ratio of 1:20 to 20:1, 1:15 to 15:1, 1:10 to 10:1, 1:9 to 9:1, 1:8 to 8:1, 1:7 to 7:1, 1:6 to 6:1, 1:5 to 5:1, 1:4 to 4:1, 1:3 to 3:1, 1:2 to 2:1, 2:3 to 3:2, or about 1:1. In a preferred embodiment, the silver core has an average diameter of 50-200 nm, preferably 60-150 nm, preferably 70-120 nm, preferably 80-110 nm, preferably 90-100 nm. The polypyrrole shell may be formed by polymerizing the aforementioned pyrrole molecules of the pyrrole-adsorbed silver nanoparticles. In a preferred embodiment, the polypyrrole shell has an average thickness of 25-80 nm, 30-70 nm, 40-65 nm, 45-60 nm, or 50-55 nm. In a preferred embodiment, the polypyrrole shell is of uniform thickness. Alternatively, the polypyrrole shell may be of non-uniform thickness. The term "uniform thickness" refers to an average shell thickness that differs by no more than 10%, no more than 5%, no more than 4%, no more than 3%, no more than 2%, preferably no more than 1% at any given location on the polypyrrole shell of the polypyrrole-coated Ag particles. The term "non-uniform thickness" may refer to an average thickness that differs by more than 10% at any given location on the polypyrrole shell.

In one or more embodiments, at least a portion of the surface of the silver core (e.g. silver nanoparticles) is coated by the polypyrrole shell, preferably greater than 50%, greater than 60%, greater than 70%, greater than 80%, greater than 90%, greater than 95%, greater than 96%, greater than 97%, greater than 98%, greater than 99%, or greater than 99.5% of the surface of the silver nanoparticles is coated by the polypyrrole shell. In at least one embodiment, each silver core (e.g. the silver nanoparticles) is encapsulated by the polypyrrole shell.

As used herein, UV-vis spectroscopy or UV-vis spectrophotometry refers to absorption spectroscopy or reflectance spectroscopy in the ultraviolet-visible spectral region. This means it uses light in the visible and adjacent (near-UV and near-infrared) ranges. The absorption or reflectance in the visible range directly affects the perceived color of the chemicals involved. In this region of the electromagnetic spectrum, molecules undergo electronic transitions. Molecules containing t-electrons or non-bonding electrons (n-electrons) can absorb the energy in the form of ultraviolet or visible light to excite these electrons to higher antibonding molecular orbitals. The more easily excited the electrons (i.e. the lower the energy gap between the HOMO and the LUMO), the longer the wavelength of light it can absorb. This technique is complementary to fluorescence spectroscopy, in that fluorescence deals with transitions from the excited state to the ground state, while absorption measures transitions from the ground state to the excited state. In one or more embodiments, the polypyrrole-coated Ag particles produced herein has an ultraviolet visible (UV-vis) absorption in a range of 350-800 nm, preferably 400-750 nm, preferably 450-700 nm, preferably 500-650 nm, preferably 550-600 nm.

Raman spectroscopy is a spectroscopic technique used to observe vibrational, rotational and other low frequency modes in a system. Raman spectroscopy is commonly used in chemistry to provide a fingerprint by which molecules can be identified. It relies on inelastic scattering, or Raman scattering, of monochromatic light, usually from a laser in the visible, near infrared, or near ultraviolet range. The laser light interacts with molecular vibrations, phonons or other excitations in the system, resulting in the energy of the laser photons being shifted up or being shifted down. The energy difference between the absorbed and emitted photon corresponds to the energy difference between two resonant states of the material and is independent of the absolute energy of the photon. The shift in energy provides information on the vibrational modes in the system.

As a particular subset within the realm of Raman spectroscopy, surface enhanced Raman spectroscopy or surface enhanced Raman scattering (SERS) refers to a surface sensitive technique that enhances Raman scattering by molecules adsorbed on rough metal surfaces. SERS refers to the observation that certain molecules adsorbed on specially prepared metallic surfaces possess Raman spectrum of greatly increased intensity. Under external radiation an "active site", "magic site", or "hot spot" appears at junctions of or in the vicinity of particles corresponding to the phenomenon of localized surface plasmon resonances (LSPRs) mediating intense electromagnetic (EM) field distribution. There are two primary theories to the mechanism of the enhancement effect of SERS. The electromagnetic theory proposes the excitation of localized surface plasmons, while the chemical theory proposes the formation of charge-transfer complexes. In the electromagnetic theory, the increase in intensity of the Raman signal for adsorbates on particular surfaces occurs because of an enhancement in the electric field provided by the metallic surface.

According to a second aspect, the present disclosure relates to a surface enhanced Raman scattering (SERS) active substrate, comprising a glass layer and polypyrrole-coated Ag particles immobilized on the glass layer. In one embodiment, the polypyrrole-coated silver nanoparticles are produced by the method of the first aspect of the present disclosure, which involves mixing silver nanoparticles with an aqueous solution of pyrrole to produce a mixture comprising pyrrole-adsorbed silver nanoparticles, and mixing an oxidizing agent with the mixture to polymerize the pyrrole of the pyrrole-adsorbed silver nanoparticles thereby forming the polypyrrole-coated Ag particles. Thus, the polypyrrole-coated Ag particles of the surface enhanced Raman scattering (SERS) active substrate may have sizes, dimensions, core-shell architectures and properties as those previously described. In certain embodiments, the sizes, dimensions, core-shell architectures and properties of the polypyrrole-coated Ag particles may vary from aforementioned ranges and the polypyrrole-coated Ag particles may still function as intended and/or possess the intended SERS activity.

The surface enhanced Raman scattering (SERS) active substrate of the present disclosure comprises a glass layer. The nature of this layer is not viewed as particularly limiting and any suitable material of varying size, shape and texture (i.e. smooth, porous, roughened, corrugated and/or etched) may be envisioned that is non-conductive and provides suitable SERS activity. In a preferred embodiment, the layer is inert, preferably inert such as glass or silicon, preferably glass.

The surface enhanced Raman scattering (SERS) active substrate also comprises the polypyrrole-coated Ag particles immobilized on the glass layer. In one embodiment, the polypyrrole-coated Ag particles are non-agglomerated. For example, the polypyrrole-coated Ag particles are discrete and separated by interparticle gaps or an interparticle distance of 0.5-100 nm, preferably 1-80 nm, preferably 2-60 nm, preferably 3-40 nm, preferably 4-20 nm, preferably 5-15 nm, most preferably 6-10 nm. The interparticle distance refers to the shortest distance between the outer edges of two neighboring polypyrrole-coated Ag particles. The properties of polypyrrole-coated Ag particles may change when particles aggregate and these interparticle gaps provide the hot spots or active sites for SERS enhancement. In a preferred embodiment, the polypyrrole-coated Ag particles of the present disclosure have an average interparticle distance of less than 200% of their average particle size, preferably less than 150% of their average particle size, preferably less than 100% of their average particle size, preferably less than 50% of their average particle size, preferably less than 25% of their average particle size, preferably less than 10% of their average particle size, preferably less than 5% of their average particle size. For example, spherical polypyrrole-coated Ag particles having a 200 nm diameter may be separated by an average interparticle distance of 10-400 nm, preferably 10-200 nm, preferably 10-100 nm, preferably 10-20 nm.

In one or more embodiments, the surface enhanced Raman scattering (SERS) active substrate further contains additional nanoparticles comprising at least one metal selected from the group consisting of gold, copper, aluminum, platinum, palladium, and alloys thereof immobilized on the glass layer. These metals are considered SERS active metals capable of surface plasmon resonance under light from 200-1100 nm. The additional nanoparticles may be randomly or non-randomly located amongst the polypyrrole-coated Ag particles of the present disclosure. In a preferred embodiment, a weight ratio of the additional nanoparticles to the polypyrrole-coated Ag particles is less than 1:1, preferably less than 2:3, preferably less than 3:7, preferably less than 1:3, preferably less than 1:4, preferably less than 1:8, preferably less than 1:9.

In a preferred embodiment, the polypyrrole-coated Ag particles and the additional nanoparticles comprising at least one metal selected from the group consisting of gold, copper, aluminum, platinum, palladium, and alloys thereof are immobilized on the glass substrate by adsorption defined as the adhesion of atoms, ions or molecules to a surface creating a film of polypyrrole-coated Ag particles and additional nanoparticles immobilized on the glass layer. The exact nature of the adsorption depends on the details of the species involved but the process can generally be classified physisorption (characteristic of weak van der Waals forces) or chemisorption (characteristic of covalent bonding) or due to electrostatic attraction. As used herein, "immobilized" or "immobilizing" refers to the adsorption and/or chemical binding via strong atomic bonds (e.g. ionic, metallic and covalent bonds) and/or weak bonds such as van der Waals interactions and hydrogen bonds. In a preferred embodiment, the polypyrrole-coated Ag particles and the additional nanoparticles are physisorbed onto the glass layer, leaving the chemical species of these materials intact.

Immobilizing of the polypyrrole-coated Ag particles and the additional nanoparticles onto the glass layer may be accomplished by the Langmuir-Blodgett technique, sedimentation, and/or evaporation induced adsorption. In one embodiment, the surface enhanced Raman scattering (SERS) active substrate of the present disclosure may be prepared by wet chemistry techniques using a "drop and dry" method. In a preferred embodiment, the "drop and dry" method involves washing glass slides with an alcohol in an ultrasonic bath for up to 2 hours, preferably up to 1 hour, preferably up to 45 min, preferably up to 30 min, preferably up to 20 min, preferably up to 15 min, preferably up to 10 min, preferably up to 5 min. In terms of the present disclosure, suitable alcohols may include, but are not limited to, methanol, ethanol, propanol, isopropanol, and butanol. Other polar protic solvents such as water or polar aprotic solvents such as acetone may be used in addition to or in lieu of the alcohols.

The "drop and dry" method may also involve the step of transferring an aqueous suspension of the polypyrrole-coated Ag particles and the additional nanoparticles onto the washed glass slides. In one embodiment, the polypyrrole-coated Ag particles are present in the aqueous suspension at a concentration of 0.01-100 mg/mL, preferably 0.05-50 mg/mL, preferably 0.1-25 mg/mL, preferably 0.5-10 mg/mL, preferably 1-5 mg/mL. In one embodiment, the aqueous suspension has a particle concentration of 100-10,000 particles/mL, preferably 250-5,000, preferably 500-4,000, preferably 1,000-3,000, preferably 1,500-2,500 particles/mL. In one embodiment, the aqueous suspension has a silver mass percentage by weight of 0.005%-10%, preferably 0.01-5%, preferably 0.05-1%, preferably 0.1-0.5%. The amount of the aqueous suspension transferred onto the glass slide may be in a range from 0.1-100 mL, 0.4-50 mL, or 1-10 mL. However, depending on the size of the glass slide, the amount of the aqueous suspension transferred may be less than 0.1 mL or greater than 100 mL. Alternatively, the aqueous suspension of the polypyrrole-coated Ag particles and the additional nanoparticles may be transferred onto the washed glass slides by immersing the glass slides in the aqueous suspension.

The "drop and dry" method may further involve the step of drying the glass slides after the transferring or immersing step to produce surface enhanced Raman scattering (SERS) active substrates. Preferably this step involves the removal of water and other solvents from the aqueous suspension, and coordinated solvents may also be removed. In one embodiment, this step involves leaving the glass slides in air at room temperature (e.g. 10-35° C., 15-30° C., or 20-25° C.) to evaporate the water. In another embodiment, the glass slides may be heated in an oven at a temperature of 60-150° C., 70-100° C., or 80-90° C. to remove the water and other solvents. Alternatively, the glass slides may be subjected to a vacuum, an air flow, or an inert gas flow during the drying step.

It is envisaged that the method to produce surface enhanced Raman scattering (SERS) active substrate of the present disclosure is not particularly limiting and may be adapted to incorporate a variety of methods including, but not limited to, ion implantation, wet chemistry, physical vapor deposition, lithography (e.g. nanolithography) and mixtures thereof.

As used herein, the SERS "enhancement factor" refers to the extent that surface enhancement increases the intensity of Raman scattering. In a preferred embodiment, the SERS enhancement factor refers to the analytical enhancement factor (AEF). The AEF can be calculated given that $C_{RS}$ and $C_{SERS}$ are the concentrations detected for non-SERS and SERS activity, respectively, $I_{RS}$ is the Raman intensity produced for a concentration under non-SERS conditions and $I_{SERS}$ is the Raman intensity for a concentration under SERS substrate activity using equation (I):

$$AEF = \frac{C_{RS} I_{SERS}}{C_{SERS} I_{RS}} \qquad (I)$$

In one or more embodiments, the surface enhanced Raman scattering (SERS) active substrate of the present disclosure has a SERS enhancement factor of at least $10^4$, more preferably $10^4$-$10^{13}$, more preferably $10^5$-$10^{12}$, more preferably $10^6$-$10^{11}$, more preferably $10^7$-$10^{10}$, more preferably $10^8$-$10^9$. In another embodiment, the SERS enhancement factor may refer to the average SERS enhancement factor or SERS substrate enhancement factor (SSEF) where the SERS intensity is normalized by the number of adsorbed molecules rather than by the volume concentration in the starting solution. In another embodiment, the SERS enhancement factor may refer to the single-molecule enhancement factor (SMEF).

According to a third aspect, the present disclosure relates to a method for measuring surface enhanced Raman scattering (SERS) signal of an analyte. The method involves the steps of contacting the analyte with the surface enhanced Raman scattering (SERS) active substrate of the second aspect to prepare a sample, exciting the sample with a light source to produce a Raman signal, and detecting and measuring the Raman signal of the sample, wherein the analyte has a Raman signal that is enhanced relative to that of the analyte without the surface enhanced Raman scattering (SERS) active substrate.

As used herein, the term "analyte" refers to a chemical or biological entity that can be identified, detected and/or quantified by an analytic process such as the method of measuring the surface enhanced Raman scattering (SERS) signal of the analyte described herein. In a preferred embodiment, the analyte is a chemical or biological entity that can be detected or quantified by SERS. A "biological analyte" includes, but is not limited to, microorganisms, cells, cell products, and/or biological molecules. A microorganism refers to a microscopic living system including, but not limited to, viral particles such as virions, prions, or viriods, bacteria, fungi, archae, protists, microscopic algae, plankton, planarian and mixtures thereof. A cell includes both prokaryotic and eukaryotic cells, including both natural and recombinant cells and cell products include constituents of cells such as cell membranes and organelles.

As used herein, "biological molecule" refers to a molecule that is produced by a living organism and also refers to synthetic analogs of such molecules. Examples of such biological molecules include, but are not limited to, carbohydrates such as glucose, disaccharides and polysaccharides, proteins, lipids, lipid bilayers, nucleic acids such as DNA and RNA. Biological molecules may also refer to small molecules, including monomers and oligomers of other biological molecules, i.e. nucleic acids, nucleotides, fatty acids and the like. The biological molecules may be naturally occurring or synthetic and may include both naturally occurring and synthetic portions. The term biological molecule also refers to derivative of biological molecules, such as conjugated nanoparticles. In a preferred embodiment, the analyte contains at least one biological molecule selected from the group consisting of a protein, a deoxyribonucleic acid sequence, a ribonucleic acid sequence, an amino acid, a peptide, a nucleotide, a nucleoside, and a neurotransmitter.

Dyes with strong absorptions in the visible light range and therefore in resonant conditions are an important family of SERS probes. Acidic dyes are dyes that have a negative charge causing them to bind or associate with positively charged structures; representative examples include nigrosine, picric acid, eosin, acid fuschin and the like. Basic dyes are dyes that have a positive charge causing them to bind or associate with negatively charged structures; representative examples include Rhodamine 6G, crystal violet, methylene blue, safranin, basic fuschin and the like. Neutral dyes are generally formed from precipitation in which aqueous acidic and basic dyes are combined; representative examples include eosinate of methylene blue, giesma and the like. In terms of the present disclosure, the analyte may comprise at least one dye and the dye may be acidic, basic or neutral, preferably basic, preferably Rhodamine 6G.

As used herein, Rhodamine 6G includes, but is not limited to, Rhodamine 6G chloride ($C_{28}H_{31}ClN_2O_3$), Rhodamine 6G perchlorate ($C_{28}H_{31}ClN_2O_7$), and rhodamine 6G tetrafluoroborate ($C_{28}H_{31}BF_4N_2O_3$). Rhodamine 6G dyes have an absorption maximum ($\lambda_{max}$) at around 520-530 nm and emit at around 590 nm. They are known for its photostability, high fluorescence quantum yield, low cost, and its relatively small Stokes shift. It is envisioned that other dyes may be used as the analyte in lieu of Rhodamine 6G. Suitable dyes may be selected from the group including, but not limited to, Rhodamine B, Rhodamine 101, Rhodamine 123, Sulforhodamine 101, crystal violet, methyl violet, fluorescein, prussian blue, egyptian blue, methyl blue, methylene blue, new methylene blue, han purple, potassium ferrocyanide, potassium ferricyanide, methyl violet 6B, methyl violet 2B, fuchsine, ararosaniline, ranailine, new fuchsine, magenta II, bromocresol green, malachite green, xanthene dyes (fluorescein, eosine, phloxine, eythrosine, rose bengal), benzotriazole dyes (benzotriazole BTA, benzotriazole dye 2 BTZ), anthraquinone dyes, flavone dyes, arylmethane dyes, protoberberine dyes and mixtures thereof.

The sample may be prepared by contacting the analytes with the surface enhanced Raman scattering (SERS) active substrate. As used herein, a "sample" refers to the surface enhanced Raman scattering (SERS) active substrate with the analyte completely or partially adsorbed onto the substrate. In one embodiment, the analyte is adsorbed onto at least one polypyrrole-coated Ag particle, preferably onto two or more polypyrrole-coated Ag particles. In another embodiment, the analyte are adsorbed such that at least a portion of the analyte is within or exposed to the interparticle gaps or hot spots of the surface enhanced Raman scattering (SERS) active substrate. The analyte may be adsorbed by a dip (e.g. incubation, immersion) and wash method.

The sample prepared may be excited by a light source to produce a Raman signal. The light source may be any radiation source suitable for Raman spectroscopy. In a preferred embodiment, the light source is a laser source. Exemplary laser sources include, but are not limited to, gas lasers, chemical lasers, excimer lasers, metal vapor lasers, solid state lasers, titanium sapphire lasers, fiber lasers, photonic crystal lasers, semiconductor lasers, dye lasers, and free electron lasers.

In a preferred embodiment, the radiation source may be a gas laser, preferably a helium-neon laser. A helium-neon laser or HeNe laser is a type of gas laser whose gain medium consists of a mixture of helium and neon (10:1) inside of small bore capillary tube, usually excited by a DC electrical discharge. The pressure inside the tube is 1 mm of Hg. The most widely used HeNe laser operates at a wavelength of 632.8 nm in the red part of the visible spectrum. HeNe lasers emit at several wavelengths at 543.5 nm, 593.9 nm, 611.8 nm, 632.8 nm, 1.1523 μm, 1.52 μm, 3.3913 μm. If a HeNe laser is used, it is preferably operated at 632.8 nm.

In another embodiment, the light source is an ion laser, for example a krypton or argon laser. An ion laser is a gas laser which uses an ionized gas as its lasing medium. An argon laser is one of the families of ion lasers that use a noble gas as the active medium. A krypton laser is an ion laser using krypton ions as a gain medium, pumped by electric discharge. In another embodiment, the light source is a laser diode, an electrically pumped semiconductor laser in which the active laser medium is formed by a p-n junction of a semiconductor diode. Exemplary appropriate types of laser diodes include, but are not limited to, double heterostructure lasers, quantum well lasers, quantum cascade lasers, separate confinement heterostructure lasers, distributed Bragg reflector lasers, distributed feedback lasers, vertical cavity surface emitting lasers (VCSELs), vertical external cavity surface emitting lasers (VECSELs) and external cavity diode lasers.

For the samples described herein, a laser wavelength operating in the range of 200-1100 nm allows efficient coupling to the surface enhanced Raman scattering (SERS) active substrate, preferably 300-1000 nm, preferably 400-900 nm, preferably 500-800 nm, preferably 500-700 nm, preferably 500-650 nm, preferably 600-650 nm. In a preferred embodiment, the laser exposure time is less than 10 s, preferably less than 5 s, preferably less than 4 s, preferably less than 3 s, preferably less than 2 s. In a preferred embodiment, the laser is operated at a power at the sample surface of less than 10 mW, preferably less than 8 mW, preferably less than 6 mW, preferably less than 5 mW. These parameters allow for the minimization and prevention of photodegradation of the analyte of interest.

Detecting and measuring the Raman signal of the sample may be performed by any suitable detector. Two main categories of optical detectors are used in typical SERS measurement: single channel and multichannel. Single channel detectors have just one element that accepts light through the exit slit of a monochromator or polychromator. An apparatus containing a single channel detector produces a spectrum by rotating the monochromator or polychromator grating and recording one data point for each grating position. In contrast, multichannel detectors collect many data points simultaneously without moving a grating or any other part of the spectrograph. This allows much more efficient data collection than for single channel detectors, as large amounts of spectral data can be collected in a single exposure. In terms of the present disclosure, the detector may be single channel or multichannel. Exemplary single channel detectors include, but are not limited to, a single photodiode, a photomultiplier (PMT), and an avalanche photodiode (APD). Exemplary multichannel detectors include, but are not limited to, a diode array, and a charge coupled device (CCD).

In a preferred embodiment, the Raman signal is detected and measured in the range of 200-2000 $cm^{-1}$, preferably 400-1800 $cm^{-1}$, preferably 600-1600 $cm^{-1}$, preferably 800-1400 $cm^{-1}$ depending on the analyte of interest. In a preferred embodiment, the analyte has a Raman signal that is enhanced (with regards to atomic unit intensity) $10^2$-$10^{15}$ fold relative to the Raman signal of a substantially similar analyte measured by substantially similar method without the surface enhanced Raman scattering (SERS) active substrate (i.e. on a bare glass layer), preferably $10^4$-$10^{13}$, preferably $10^5$-$10^{12}$, preferably $10^6$-$10^{11}$, preferably $10^7$-$10^{10}$ preferably $10^8$-$10^9$. This level of enhancement should be sufficient for single molecule detection applications. In one or more embodiments, the method has a surface enhanced Raman scattering (SERS) detection limit of the analyte at a concentration of $1\times10^{-1}$-$1\times10^{-6}$ M, preferably $1\times10^{-10}$-$1\times10^{-7}$, more preferably $1\times10^{-9}$-$1\times10^{-8}$. In another embodiment, the method may further comprise correlating the Raman signal from the analyte with a chemical structure of a known analyte with optional assistance of a computer.

The examples below are intended to further illustrate protocols for producing, characterizing the polypyrrole-coated Ag particles as well as the surface enhanced Raman scattering (SERS) active substrate, and uses thereof. They are not intended to limit the scope of the claims.

Example 1

Materials

Pyrrole monomer of reagent grade having the purity of 99.9%, and silver (Ag) nanoparticles from Sigma Aldrich were used without further purification. $FeCl_3$ of reagent grade (98%) was also obtained from Sigma Aldrich and used as received. The chemicals used for purification such as acetone, ethanol, and methanol were purchased locally.

Example 2

Synthetic Methods

Polypyrrole-coated (PPy-coated) Ag particles were synthesized by a facile in-situ oxidative chemical polymerization approach using pyrrole monomers in the presence of Ag nanoparticles. The chemical synthesis for the preparation of PPy-coated Ag nanoparticles is illustrated in FIG. 1. A fixed quantity of Ag nanoparticles was added to 100 mL deionized water which was set under ultrasonic vibrations for 45 min at 25° C. The formed Ag dispersion was transferred to a 0.5 L single neck flask on a magnetic stirrer. A fixed quantity of pyrrole monomers was added to the Ag dispersion. The resulting mixture was stirred continuously for 30 min to ensure adequate adsorption of pyrrole monomers on the surface of Ag particles. 2 g of $FeCl_3$ was dissolved in 100 mL demineralized water separately. The $FeCl_3$ solution was added to the pyrrole adsorbed Ag particle dispersion. Further stirring of the reaction mixture under similar reaction settings for 24 h led to the formation of PPy-coated Ag particles. The synthesized PPy-coated Ag particles were filtered and washed with deionized water to ensure the removal of unreacted oxidant. Further procedure was adopted to remove any possible forms of oligomer with careful methanol-rinse. The obtained powder was dried at 70° C. for 2 hours for characterizations.

Example 3

Characterizations

The morphology of obtained samples was measured with FE-SEM (TESCAN FERA). Quantitative elemental analysis was provided by SEM-aided EDS measurements. The FT-IR spectra were obtained by a FT-IR spectrometer (Nicolet iS50 spectrometer, Thermo Scientific, UK) within the wavenumber range of 4000-400 $cm^{-1}$ at a resolution of 1 $cm^{-1}$. Diffuse reflectance spectra (DRS) for the band gap measurement of the samples were recorded using a UV-VIS-NIR (V-730, JASCO) spectrophotometer.

To confirm the SERS-activity, PPy-coated Ag particles were immobilized on a glass substrate by the "drop and dry" technique. Approximately 400 μL aqueous solution of PPy-coated Ag particles was dropped on the glass substrate and left for dry. The as-prepared samples were incubated with Rhodamine 6G (R6G) dye at a concentration of $1\times10^{-6}$ M for ca. 10 mins and thereafter rinsed several times with DI water. Raman measurements were performed on the R6G dye, as-prepared PPy-coated Ag particles, and as-prepared R6G incubated PPy-coated Ag particles on glass using LabRAM HR Evolution Raman system. Internally aligned HeNe laser (632.8 nm) of 17 mW was filtered by 50% to avoid potential dissociation and damage to the sample. 50× long working distance lens was used to focus the excitation on the sample and scattered photons were collected in backscattering configuration for 10 sec. and accumulation of 2. The laser was turned off immediately after the signal collection.

Example 4

Surface Morphology and Structure

Figure 3A:
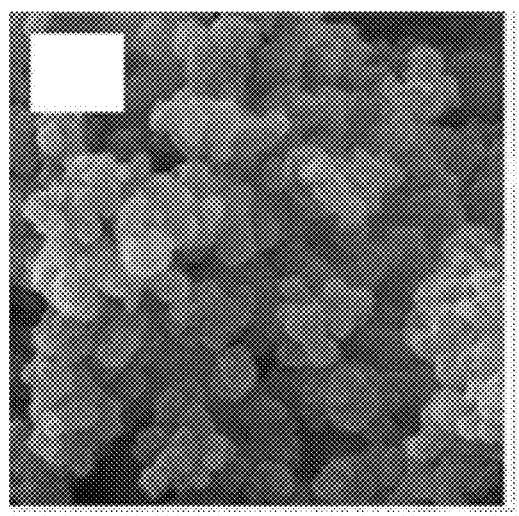
FIG. 3A is a FE-SEM image of the PPy-coated Ag particles.
Figure 3B:
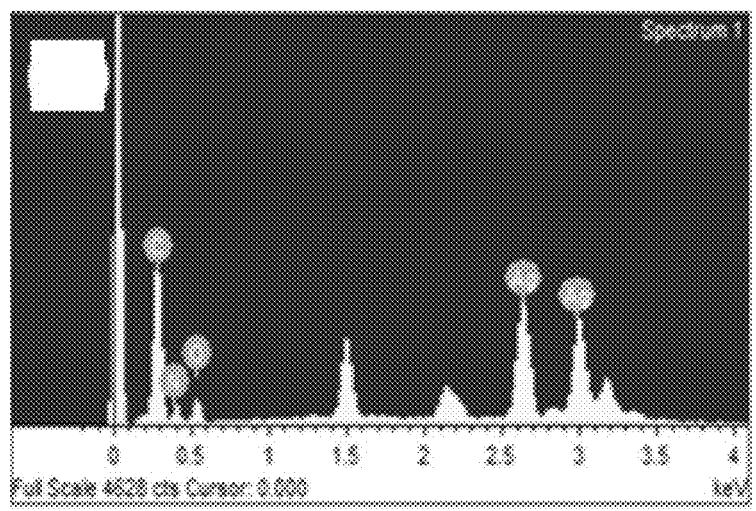
FIG. 3B is a spectrum collected by SEM aided electron dispersion spectroscopy (EDS) of the PPy-coated Ag particles of FIG. 3A.
Figure 3C:
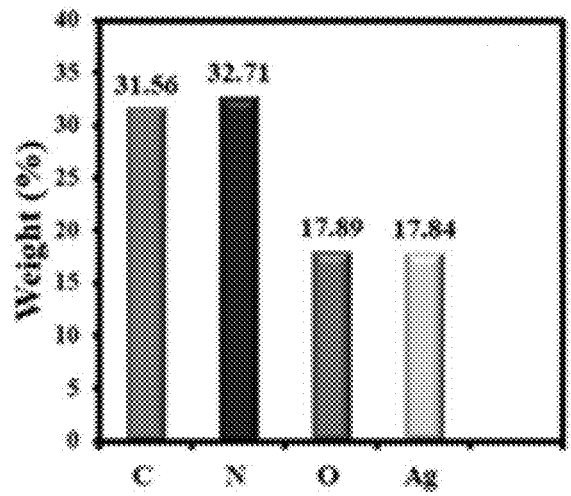
FIG. 3C is a bar graph illustrating quantitative weight percentages of elements Ag, C, N, and O of the PPy-coated Ag particles.
Figure 3D:
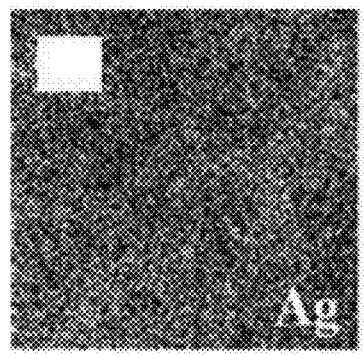
FIG. 3D shows the mapping of element Ag of the PPy-coated Ag particles.
Figure 3E:
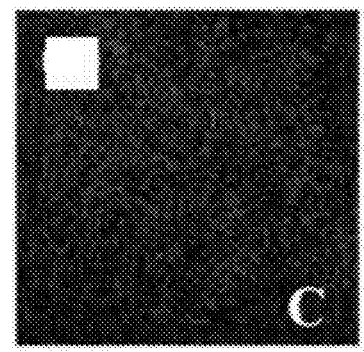
FIG. 3E shows the mapping of element C of the PPy-coated Ag particles.
Figure 3F:
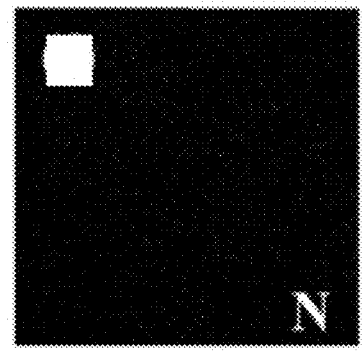
FIG. 3F shows the mapping of element N of the PPy-coated Ag particles.
Figure 3G:
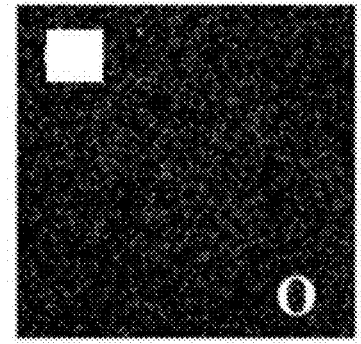
FIG. 3G shows the mapping of element O of the PPy-coated Ag particles.

The surface morphology and structure of PPy-coated Ag particles were examined by FE-SEM. FE-SEM images with different magnifications are shown in FIGS. 2A-D. Based on the images, it was observed that the granular PPy-coated Ag particles were spherical in shape with a grain size in the range of 150-200 nm. In addition to these FE-SEM images, elemental composition analysis of PPy-coated Ag particles were studied using FE-SEM-EDX and the results are shown in FIGS. 3A-G. From this analysis, it is quite clear that PPy-coated Ag particles comprise silver (Ag), carbon (C), nitrogen (N), and oxygen (O). The presence of two Ag peaks centered at the energy of 2.55 keV and 3.0 keV in addition to the C, N and O, confirms the presence of Ag in PPy-coated Ag particles (FIGS. 3B and C). It should be noted that only the presence of chemical elements could be determined based on the currently used energy dispersive X-ray analysis. Accordingly, weight percentages of elements demonstrated by FIG. 3C are non-quantitative results which only indicate the presence of each element. Moreover, the corresponding elemental mapping for PPy-coated Ag particles demonstrated by FIGS. 3D-G further confirms the presence of Ag, C, N, and O as well as the distribution of Ag, C, N, and O in PPy-coated Ag particles. Overall, FE-SEM, EDS, and elemental mapping analyses indicated that the polymerization of pyrrole monomers has taken place on the surface of Ag nanoparticles. A schematic representation depicting the synthesis of PPy-coated Ag particles can be found in FIG. 1.

Example 5

FT-IR

Figure 4A:
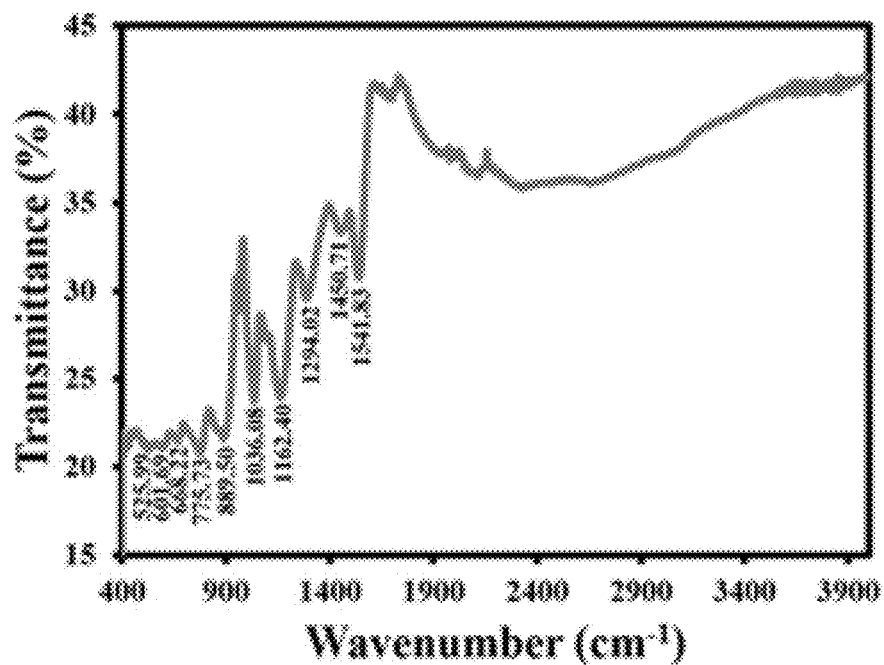
FIG. 4A is a Fourier transform Infrared (FT-IR) spectrum of the PPy-coated Ag particles.
Figure 4B:
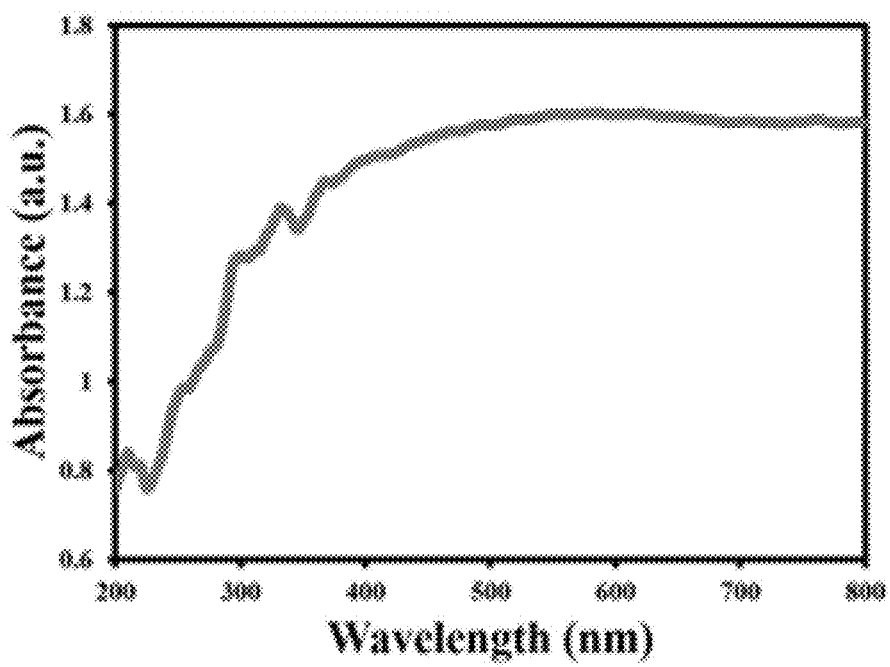
FIG. 4B is an ultraviolet-visible (UV-vis) absorption spectrum of the PPy-coated Ag particles.

FT-IR spectrum of PPy-coated Ag particles has been depicted in FIG. 4A. An absorption peak at 889.50 cm$^{-1}$ which was due to the out-of-plane deformation of C—H vibration was found at the finger print region of the FT-IR spectrum of PPy coated Ag nanoparticles, confirming the PPy formation by the polymerization of monomers. The band at 1294.02 cm$^{-1}$ was originated from the C—N in-plane vibration. The absorption frequencies at 1162.40 and 1036.08 cm$^{-1}$ were due to the C—H bending modes. The strong bands at 1541.83 and 1450.71 cm$^{-1}$ were due to stretching C—C bond vibrations of pyrrole rings. Several other peaks in the fingerprint region (600-1500 cm$^{-1}$) of the FT-IR spectrum of PPy-coated Ag particles may be assigned to the ring stretching and C—H in plane deformation modes. Additionally, peaks in the range of 700 to 400 cm$^{-1}$ were found, which could be attributed to the metal-oxygen bonding. The polymerization of pyrroles on the surface of Ag nanoparticles was confirmed by the presence of the stretching vibration of C—N at 1294.02 cm$^{-1}$. FIG. 4B is an absorption spectrum of PPy-coated Ag particles revealing that the PPy-coated Ag particles have the highest absorption in the visible region (400 nm to 800 nm).

Example 6

Raman Spectroscopy

Figure 5A:
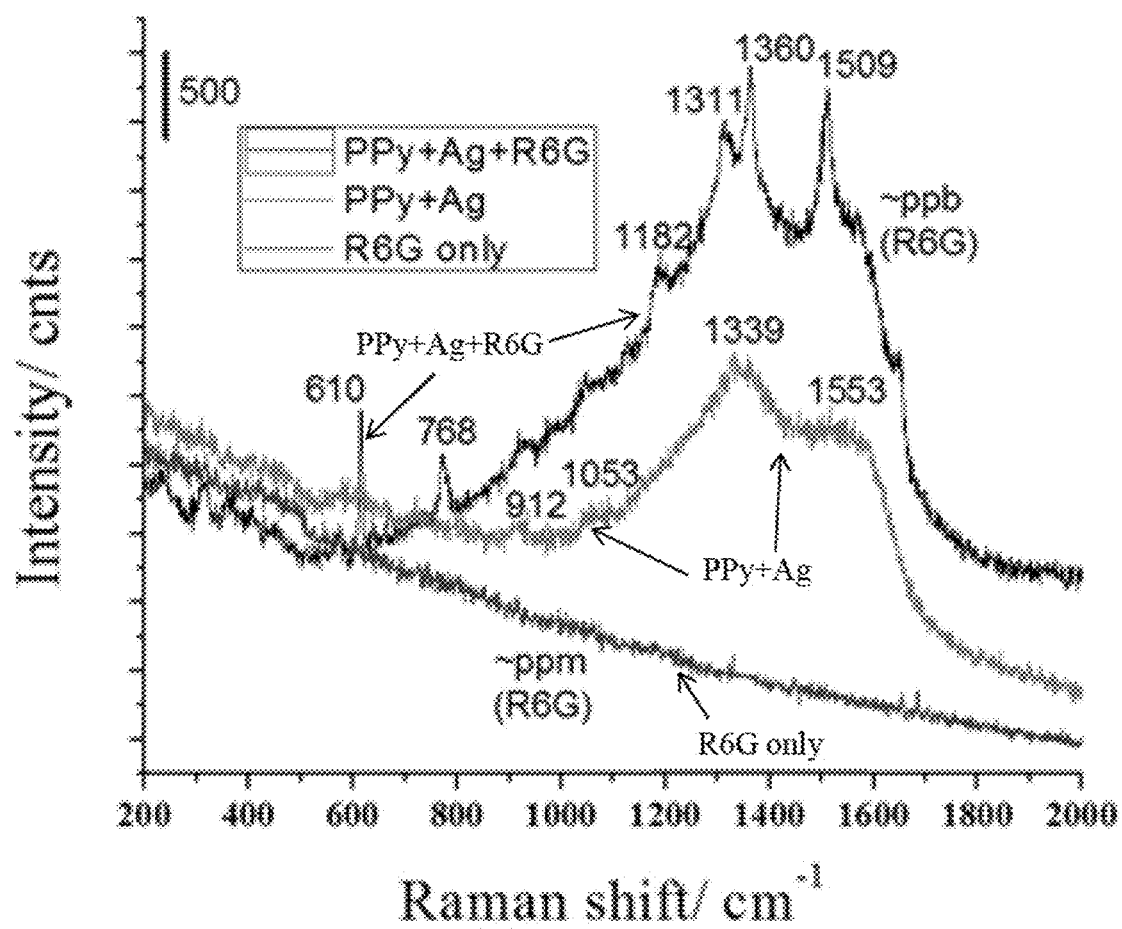
FIG. 5A is an overlay of Raman spectrum of Rhodamine 6G (R6G), surface enhanced Raman scattering (SERS) spectra of the PPy-coated Ag particles (PPy+Ag) and R6G incubated with the PPy-coated Ag particles (PPy+Ag+R6G), respectively.
Figure 5B:
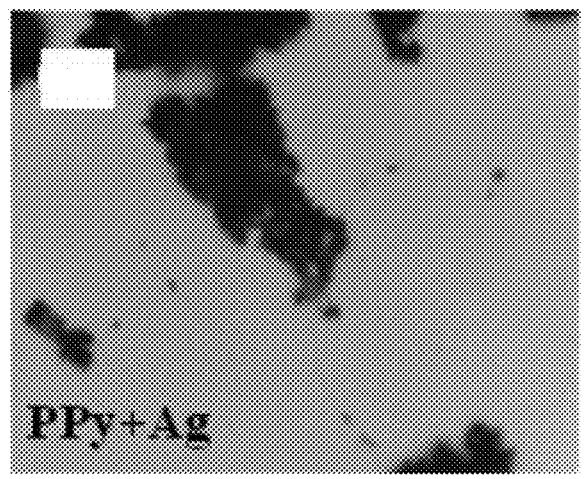
FIG. 5B is an image of the PPy-coated Ag particles (PPy+Ag) captured by a charge-coupled detector (CCD) camera.
Figure 5C:
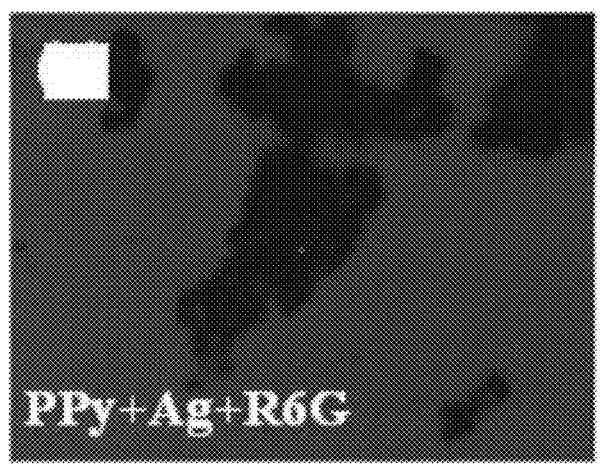
FIG. 5C is an image of R6G incubated with the PPy-coated Ag particles (PPy+Ag+R6G) captured by a CCD camera.

As reported in literature, Raman peaks of PPy were observed in the presence of Ag, although peaks were seldom observed without Ag nanoparticles [Furukawa, Y.; Tazawa, S.; Fujii, Y.; Harada, I. Raman Spectra of Polypyrrole and Its 2,5-13c-Substituted and C-Deuterated Analogues in Doped and Undoped States. Synth. Met. 1988, 24, 329-341; and Mikat, J.; Orgzall, I.; Hochheimer, H. D. Raman Spectroscopy of Conducting Polypyrrole under High Pressure. *Phys. Rev. B* 2002, 65, 174202, each incorporated herein by reference in their entirety]. One purpose of the current work was to coat Ag nanoparticles with PPy so that the particles could play a role in molecule detection while pose no environmental threat because of the protection from PPy layer. FIG. 5A shows Raman spectrum of R6G dye, as well as SERS spectra of PPy and PPy-coated Ag particles, respectively. FIGS. 5B-C each represent the CCD images of the specimen, PPy-coated Ag particles and R6G incubated PPy-coated Ag nanoparticles, respectively, viewed at the experimental focus. SERS peaks of PPy at 912, 1053, 1339, 1553 wavenumber were attributed to ring deformation, symmetrical CH-in-plane bending, C6 ring bending, and C=C stretching mode, respectively [Furukawa, Y.; Tazawa, S.; Fujii, Y.; Harada, I. Raman Spectra of Polypyrrole and Its 2,5-13c-Substituted and C-Deuterated Analogues in Doped and Undoped States. Synth. Met. 1988, 24, 329-341; and Mikat, J.; Orgzall, I.; Hochheimer, H. D. Raman Spectroscopy of Conducting Polypyrrole under High Pressure. *Phys. Rev. B* 2002, 65, 174202, each incorporated herein by reference in their entirety]. No peaks were observed in the sample of R6G at a concentration of 1×10$^{-6}$ M, as shown in the bottom spectrum. However, the PPy-coated Ag particles incubated with R6G dye at a concentration of 1×10$^{-9}$ M evidently showed a strong enhancement in SERS signal of the dye. The peaks observed therein on the top of PPy Raman spectrum confirmed the fingerprints of R6G reported so far in numerous attempts. The SERS peaks of R6G at 610, 768, 1182, 1311, 1360, and 1509 wavenumber were attributed to C—C—C ring, C—H op bend, C—C stretching, aromatic C—C stretching, aromatic C—C stretching, and aromatic C—C stretching, respectively. It is noteworthy that the background fluorescence signal was enhanced in the presence of Ag nanoparticles.

It is well-understood that electromagnetic (EM) enhancement mechanism contributes dominantly in SERS studies with an enhancement factor of 6 to 8 orders or higher [Hossain, M. K.; Kitajima, M.; Imura, K.; Okamoto, H. Interstitial-Dependent Enhanced Photoluminescence: A Near-Field Microscopy on Single Spheroid to Dimer, Tetramer, and Few Particles Gold Nanoassembly. *J. Phys. Chem. C* 2017, 121 (4); Kim, S.; Imura, K.; Lee, M.; Narushima, T.; Okamoto, H.; Jeong, D. H. Strong Optical Coupling between Mutually Orthogonal Plasmon Oscillations in a Silver Nanosphere-Nanowire Joined System. *Phys. Chem. Chem. Phys.* 2013, 15 (12), 4146-4153; and Hossain, M. K.; Shimada, T.; Kitajima, M.; Imura, K.; Okamoto, H. Near-Field Raman Imaging and Electromagnetic Field Confinement in the Self-Assembled Monolayer Array of Gold Nanoparticles. *Langmuir* 2008, 24 (17), each incorporated herein by reference in their entirety]. The electromagnetic fields need to be localized to enhance low cross-section Raman photons of the target analyte. Therefore, an effective SERS-active substrate needs to facilitate EM field localization in close proximity to the active nanoparticles. In the current investigation, it has been observed that PPy-coated Ag particles were in close proximity and had a strong affinity to target analytes. FESEM observation revealed that the thickness of PPy layer was around 50-60 nm and the diameter of Ag nanoparticles was 80-100 nm. Because of the conducting nature of PPy and band energy matching between wide band gap of PPy and that of Ag (4.27 eV), coating thickness had negligible influence on PPy-coated Ag particles [Budhiraja, N.; Sharma, A.; Dahiya, S.; Parmar, R.; Vidyadharan, V. Synthesis and Optical Characteristics of Silver Nanoparticles on Different Substrates. *Int. Lett. Chem. Phys. Astron.* 2013, 19, 80-88; and Kaloni, T. P.; Schreckenbach, G.; Freund, M. S. Band Gap Modulation in Polythiophene and Polypyrrole-Based Systems. *Sci. Rep.* 2016, 6 (November), 1-18, each incorporated herein by reference in their entirety]. Instead, the PPy coating provided a smooth channel to activate target analyte through surface plasmon polaritons that is originated in the active Ag nanoparticles. As a result, both the fluorescence and Raman signals were found to be enhanced in the presence of PPy-coated Ag particles.

Example 7

Conducting polymer itself is not considered as a good SERS-active substrate. However, such polymer coated noble metal particles, particularly PPy-coated Ag nanoparticles was found to carry efficient SERS activities. An emerging strategy was developed to coat Ag nanoparticles using conducting polymers such as PPy. SEM observation revealed a PPy coating of 50-60 nm around a silver nanoparticle having a diameter of 80-100 nm. Further characterizations through SEM-aided EDS, FT-IR, as well as UV-Vis absorption spectroscopies provided solid support herewith. The as-synthesized PPy-coated Ag particles were used to verify SERS-activity using a target molecule, R6G. The core-shell nanoparticles showed strong enhancement in SERS signals of R6G and a detection limit as low as 1×10$^{-9}$ M was achieved. At the same time, enhancement in fluorescence background signals was observed, which led to a plausible mechanism explaining why and how PPy-coated Ag nanoparticles facilitate the enhanced detection of target analytes.

The invention claimed is:

1. A method of producing polypyrrole-coated Ag particles, the method comprising:
mixing silver nanoparticles with an aqueous solution of pyrrole to form a mixture comprising pyrrole-adsorbed silver nanoparticles; and
mixing an oxidizing agent with the mixture to polymerize the pyrrole of the pyrrole-adsorbed silver nanoparticles thereby forming the polypyrrole-coated Ag particles,
wherein:
the polypyrrole-coated Ag particles are in the form of spheres; and
the polypyrrole-coated Ag particles comprise a silver core and a polypyrrole shell, and wherein at least a portion of the surface of the silver core is coated by the polypyrrole shell.

2. The method of claim 1, wherein the pyrrole is polymerized at 4-40° C.

3. The method of claim 1, wherein a molar ratio of the pyrrole to the silver nanoparticles is 5:1 to 150:1.

4. The method of claim 1, wherein the oxidizing agent is $FeCl_3$.

5. The method of claim 4, wherein a molar ratio of $FeCl_3$ to the silver nanoparticles is 5:1 to 150:1.

6. The method of claim 1, further comprising drying the polypyrrole-coated Ag particles at a temperature of 50-100° C.

7. The method of claim 1, wherein the silver core has an average diameter of 50-200 nm, and wherein the polypyrrole shell has an average thickness of 25-80 nm.

8. The method of claim 1, wherein the polypyrrole-coated Ag particles are not angular shaped.

9. The method of claim 1, wherein the polypyrrole-coated Ag particles have an average diameter of 100-360 nm.

10. The method of claim 1, wherein the polypyrrole-coated Ag particles have an UV-vis absorption of 350-800 nm.

11. The method of claim 1, wherein the mixture is devoid of polyvinyl pyrrolidone.

12. A surface enhanced Raman scattering (SERS) active substrate, comprising:
a glass layer; and
polypyrrole-coated Ag particles immobilized on the glass layer,
wherein the polypyrrole-coated Ag particles are in the form of spheres, and comprise a silver core with a diameter of 50-200 nm and a polypyrrole shell with a thickness of 25-80 nm, and wherein at least a portion of the surface of the silver core is coated by the polypyrrole shell.

13. The surface enhanced Raman scattering (SERS) active substrate of claim 12, which has a SERS enhancement factor of $10^4$-$10^{10}$.

14. The surface enhanced Raman scattering (SERS) active substrate of claim 12, wherein the polypyrrole-coated Ag particles are produced by a method comprising:
mixing silver nanoparticles with an aqueous solution of pyrrole to produce a mixture comprising pyrrole-adsorbed silver nanoparticles; and
mixing an oxidizing agent with the mixture to polymerize the pyrrole of the pyrrole-adsorbed silver nanoparticles thereby forming the polypyrrole-coated Ag particles.

15. The surface enhanced Raman scattering (SERS) active substrate of claim 12, further comprising nanoparticles comprising at least one metal selected from the group consisting of gold, copper, aluminum, platinum, palladium, and alloys thereof immobilized on the glass layer.

16. A method for measuring surface enhanced Raman scattering (SERS) signal of an analyte, the method comprising:
contacting the analyte with the surface enhanced Raman scattering (SERS) active substrate of claim 12 to prepare a sample;
exciting the sample with a light source to produce a Raman signal; and
detecting and measuring the Raman signal of the sample;
wherein the analyte has a Raman signal that is enhanced relative to that of the analyte without the surface enhanced Raman scattering (SERS) active substrate.

17. The method of claim 16, wherein the analyte comprises at least one biological molecule selected from the group consisting of a protein, a deoxyribonucleic acid sequence, a ribonucleic acid sequence, an amino acid, a peptide, a nucleotide, a nucleoside, and a neurotransmitter.

18. The method of claim 16, wherein the analyte comprises at least one synthetic molecule.

19. The method of claim 18, wherein the analyte comprises Rhodamine 6G.

20. The method of claim 16, which has a surface enhanced Raman scattering (SERS) detection limit of the analyte at a concentration of $1\times10^{-10}$-$1\times10^{-8}$ M.

* * * * *